US012622789B2

(12) United States Patent
Perryman et al.

(10) Patent No.: US 12,622,789 B2
(45) Date of Patent: May 12, 2026

(54) BLADED SPINAL FUSION IMPLANTS

(71) Applicant: Choice Spine, LLC, Knoxville, TN (US)

(72) Inventors: John Abraham Perryman, Knoxville, TN (US); Connor Michael Purviance, Knoxville, TN (US)

(73) Assignee: CHOICE SPINE, LLC, Knoxville, TN (US)

( * ) Notice: Subject to any disclaimer, the term of this patent is extended or adjusted under 35 U.S.C. 154(b) by 334 days.

(21) Appl. No.: 18/218,776

(22) Filed: Jul. 6, 2023

(65) Prior Publication Data

US 2023/0355396 A1 Nov. 9, 2023

Related U.S. Application Data

(63) Continuation of application No. PCT/US2021/012910, filed on Jan. 11, 2021.

(51) Int. Cl.
*A61F 2/44* (2006.01)

(52) U.S. Cl.
CPC ............ *A61F 2/447* (2013.01); *A61F 2/4455* (2013.01)

(58) Field of Classification Search
CPC .......... A61F 2/44; A61F 2/442; A61F 2/4455; A61F 2/446; A61F 2/4465; A61F 2/447; A61F 2002/30428; A61F 2002/30481; A61F 2002/30482; A61F 2002/30528
See application file for complete search history.

(56) References Cited

U.S. PATENT DOCUMENTS

| | | | | |
|---|---|---|---|---|
| 8,641,766 | B2 * | 2/2014 | Donner ................... | A61F 2/442 |
| | | | | 606/279 |
| 9,408,715 | B2 * | 8/2016 | Donner ................... | A61B 17/92 |
| 9,517,144 | B2 * | 12/2016 | McAtamney ....... | A61F 2/30749 |
| 9,925,059 | B2 * | 3/2018 | Chataigner ............. | A61F 2/447 |

(Continued)

FOREIGN PATENT DOCUMENTS

| | | | | |
|---|---|---|---|---|
| EP | 2716261 A1 | 4/2014 | | |
| WO | WO-2010121028 A2 * | 10/2010 | ............ | A61F 2/4611 |

(Continued)

OTHER PUBLICATIONS

Floret, Beraud, Extended European Search Report for Application No. 21918001, filed Sep. 13, 2024, 15 pages, European Patent Office, Munich Germany. The is the EPO version of the present application with amended claims.

(Continued)

*Primary Examiner* — Eric S Gibson
(74) *Attorney, Agent, or Firm* — Kevin E Flynn; FLYNN IP LAW

(57) ABSTRACT

A fusion implant which already has a cephalad anchor blade and a caudal anchor blade which are both held in a non-deployed position for delivery between a cephalad vertebra and a caudal vertebra. Positioning the fusion implant between the cephalad vertebra and the caudal vertebra while the cephalad anchor blade and the caudal anchor blade are both held in the non-deployed position. Advancing the anchor blades to engage the vertebrae. Using a cephalad locking cam to lock the cephalad anchor blade in the deployed position and using a caudal locking cam to lock the caudal anchor blade in the deployed position.

43 Claims, 16 Drawing Sheets

(56)                    References Cited

U.S. PATENT DOCUMENTS

| | | | | |
|---|---|---|---|---|
| 10,245,157 | B2 * | 4/2019 | Chataigner | A61F 2/4425 |
| 10,398,565 | B2 * | 9/2019 | Bender | A61F 2/4455 |
| 10,456,268 | B2 | 10/2019 | Mercier | |
| 2010/0168798 | A1 * | 7/2010 | Clineff | A61C 8/0012 |
| | | | | 606/279 |
| 2011/0098747 | A1 * | 4/2011 | Donner | A61F 2/4455 |
| | | | | 606/264 |
| 2011/0230971 | A1 * | 9/2011 | Donner | A61B 17/846 |
| | | | | 606/246 |
| 2013/0226300 | A1 * | 8/2013 | Chataigner | A61F 2/4455 |
| | | | | 623/17.16 |
| 2015/0209089 | A1 * | 7/2015 | Chataigner | A61F 2/4611 |
| | | | | 623/17.16 |
| 2015/0305887 | A1 * | 10/2015 | McAtamney | A61F 2/4611 |
| | | | | 623/17.16 |
| 2016/0058564 | A1 | 3/2016 | Zappacosta | |
| 2016/0256292 | A1 | 9/2016 | Donaldson | |
| 2017/0304080 | A1 | 10/2017 | Lee | |
| 2018/0303623 | A1 * | 10/2018 | Shoshtaev | A61F 2/447 |
| 2019/0274841 | A1 | 9/2019 | Hawkes | |
| 2020/0375751 | A1 * | 12/2020 | Dinville | A61F 2/442 |
| 2023/0355396 | A1 * | 11/2023 | Perryman | A61F 2/447 |

FOREIGN PATENT DOCUMENTS

| | | | | |
|---|---|---|---|---|
| WO | | 2017205623 | A1 | 11/2017 |
| WO | | WO-2022150046 | A1 * | 7/2022 ............. A61F 2/447 |

OTHER PUBLICATIONS

Han, Inho, PCT Written Opinion of the International Searching Authority for International Applciation No. PCT/US2021/012910, Oct. 6, 2021, 6 pages, Korean Intellectual Property Office, Daejeon, South Korea—(Written Opinion for parent application).

Additive Manufacturing Sparks Breakthroughs for ChoiceSpine™ Devices found at https://choicespine.com/additive-manufacturing-sparks-breakthroughs-for-choicespine-devices/ Apr. 23, 2020, 3 pages, ChoiceSpine LLC, Knoxville, Tennessee, United States of America.

Coalition MIS® ACDF Spacer _ Globus Medical. Sep. 24, 2020, 6 pages, Globus Medical, Audubon, Pennsylvania, United States of America.

Coalition MIS™ ACDF System, 2016, 62 pages, Globus Medical, stored Sep. 18, 2020, Audubon, Pennsylvania, United States of America.

Inside Electron Beam Melting, stored Sep. 18, 2020, 10 pages, GE Additive a business division of General Electric which is based in Boston, Massachusetts, United States of America.

* cited by examiner

| 1004 | Open a container having a pre-assembled fusion implant 100 with anchor blades held in a position for delivery of the fusion implant. |

↓

| 1008 | Position the fusion implant 100 between two adjacent vertebrae while the anchor blades are held in the position for delivery of the fusion implant. |

↓

| 1012 | Advance the anchor blades into the deployed position. |

↓

| 1016 | Rotate the locking cam 500 to the locked position to lock the anchor blades in the deployed position. |

904

908

450  200  110

204

450

450

920

BLADED SPINAL FUSION IMPLANTS

BACKGROUND

This application claims priority to commonly assigned and co-pending PCT Application No. PCT/US2021/012910 for Bladed Spinal Fusion Implants which was filed Jan. 11, 2021. The '910 application is incorporated by reference in its entirety.

Field of the Disclosure

This disclosure relates generally to spinal implants used for fusion of two adjacent vertebrae. More particularly this disclosure relates to spinal implants with anchor blades that are inserted into the vertebral endplates adjacent to the inserted spinal implant.

Related Art

The wonder of the operation of a healthy human spine and the utility of fusion implants to treat problems in a human spine have been covered in countless prior patent applications. One recent example is commonly assigned to the applicant for this application, Choice Spine, LLC; it is U.S. Pat. No. 10,398,565 for Limited Profiled Intervertebral Implant with Incorporated Fastening and Locking Mechanism. The text of the '565 application is incorporated by reference here in its entirety. As shown in FIG. 1, an embodiment from the '565 patent is a spinal implant 50 suitable for use in spinal fusion which has an initial position. In the initial position, the distal tips 54 of the cephalad anchor blade 58 and the distal tip 62 of the caudal anchor blade 66 are both in a retracted position. This initial position can be called the delivery position as this is the position of the blades during delivery of the spinal implant 50 into the intervertebral space.

FIG. 2 shows the spinal implant 50 after delivery into the intervertebral space and deployment of the cephalad anchor blade 58 and caudal anchor blade 66 through the cortical bone endplates of the adjacent vertebrae. This second position may be called the deployed position. One of skill in the art will appreciate that driving the distal tips 54 and 62 of the anchor blades 58 and 66 will require considerable force. It would be desirable to have the anchor blades 58 and 62 substantially surrounded in a pair of tunnel sleeves in the implant body 70 while significant force is applied to drive the distal tips 54 and 62 through the cortical bone. State of the art machining tools require lateral access to create precise curvatures. Thus, implant body 70 has a pair of guide channels to hold and guide the curved anchor blades 58 and 62 rather than a pair of guide tunnels to hold and guide the curved anchor blades 58 and 66. The difference between a guide channel and a guide tunnel is that a guide tunnel provides 360-degree encirclement of the anchor blade for at least a portion of the guide tunnel.

Vocabulary

Or.

Unless explicit to the contrary, the word "or" should be interpreted as an inclusive or rather than an exclusive or. Thus, the default meaning of or should be the same as the more awkward and/or.

Proximal and Distal.

Proximal and distal should be considered relative to the surgeon. The distal portion of a device would be the end of the device that is initially inserted into the patient's body and is thus away from the surgeon. The proximal end of the device would be the trailing end of the device away from the distal end of the device and would be closer to the surgeon during the insertion of the device.

Set.

Unless explicit to the contrary, the word "set" should be interpreted as a group of one or more items.

Gne and Gnes.

To avoid the awkward he/she and his/her or the potentially confusing singular use of they and their, this application uses the gender-neutral pronoun gne and the possessive gnes.

Step.

The term step may be used in descriptions within this disclosure. For purposes of clarity, one distinct act or step may be discussed before beginning the discussion of another distinct act or step. The term step should not be interpreted as implying any particular order among or between various steps disclosed unless the specific order of individual steps is expressly indicated.

Substantially.

Frequently, when describing an industrial process it is useful to note that a given parameter is substantially met. Examples may be substantially parallel, substantially perpendicular, substantially uniform, and substantially flat. In this context, substantially X means that for purposes of this industrial process it is X. So something that may not be absolutely parallel but is for all practical purposes parallel, is substantially parallel. Likewise, mixed air that has substantially uniform temperature would have temperature deviations that were inconsequential for that industrial process.

As recognized in C. E. Equipment Co. v. United States, 13 U.S.P.Q.2d 1363, 1368 (Cl. Ct. 1989), the word "substantially" in patent claims gives rise to some definitional leeway—thus the word "substantially" may prevent avoidance of infringement by minor changes that do not affect the results sought to be accomplished.

SUMMARY OF THE DISCLOSURE

Aspects of the teachings contained within this disclosure are addressed in the claims submitted with this application upon filing. Rather than adding redundant restatements of the contents of the claims, these claims should be considered incorporated by reference into this summary.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provided below as one of skill in the art will recognize that inventive concepts illustrated in various examples can be combined together in order to address a specific application.

Some aspects of the present disclosure can be summarized as a fusion implant with pre-assembled anchor blades for delivery between adjacent vertebrae while the anchor blades are in a delivery position. The fusion implant having:

an implant body;

a cephalad anchor blade;

a caudal anchor blade; and

a set of at least one locking cam rotatably engaged with the implant body;

The implant body having:

a proximal face:

a distal face opposite the proximal face;

a cephalad face;

a caudal face opposite the cephalad face;

a right face between the proximal face and the distal face and between the cephalad face and the caudal face;

a left face opposite the right face and between the proximal face and the distal face and between the cephalad face and the caudal face.

The cephalad anchor blade having:

a cephalad distal tip for penetration into cortical bone;

a cephalad proximal end having a cephalad lock plane for use in locking the cephalad anchor blade in a deployed position; and a cephalad stop plane facing distally which prevents the cephalad proximal end from traveling beyond the proximal face of the implant body into an interior of the implant body.

The cephalad distal tip and the cephalad proximal end located along a cephalad curved path such that the cephalad distal tip may be inserted into a cephalad blade sleeve tunnel at the proximal face and travel through the cephalad blade sleeve tunnel in the implant body to emerge from a cephalad sleeve tunnel egress opening on the cephalad face of the fusion implant and continue moving on the cephalad curved path until the cephalad stop plane contacts the proximal face of the fusion implant. The cephalad anchor blade held in a delivery position pending delivery between adjacent vertebrae.

Application of sufficient pressure on the proximal end of the cephalad anchor blade is adequate to overcome a first interaction between the cephalad anchor blade and the implant body and cause a portion of the cephalad anchor blade to move through the cephalad anchor blade egress opening.

The caudal anchor blade comprising:

a caudal distal tip for penetration into cortical bone;

a caudal proximal end having a caudal lock plane for use in locking the caudal anchor blade in a deployed position; and a caudal stop plane facing distally which prevents the caudal proximal end of the caudal anchor blade from traveling beyond the proximal face of the implant body into the interior of the implant body.

The caudal distal tip and the caudal proximal end located along a caudal curved path such that the caudal distal tip may be inserted into a caudal blade sleeve tunnel at the proximal face and travel through the caudal blade sleeve tunnel in the implant body to emerge from a caudal sleeve tunnel egress opening on the caudal face of the fusion implant and continue moving on the caudal curved path until the caudal stop plane contacts the proximal face of the fusion implant. The caudal anchor blade held in a delivery position pending delivery between adjacent vertebrae;

Application of sufficient pressure on the proximal end of the caudal anchor blade is adequate to overcome a second interaction between the caudal anchor blade and the implant body and cause a portion of the caudal anchor blade to move through the caudal anchor blade egress opening;

The set of at least one locking cam having a delivery position wherein the set of at least one locking cam does not limit:

movement of the cephalad anchor blade; or movement of the caudal anchor blade.

The set of at least one locking cam also having a locking position wherein:

the cephalad anchor blade that is in the deployed position cannot move the cephalad proximal end in a proximal direction away from the proximal face of the implant body; and the caudal anchor blade that is in the deployed position cannot move the caudal proximal end in a proximal direction away from the proximal face of the implant body.

Ideally the fusion implant is created using additive manufacturing so that the cephalad blade sleeve tunnel substantially surrounds a portion of the cephalad anchor blade within the implant body. Likewise the caudal blade sleeve tunnel substantially surrounds a portion of the caudal anchor blade. In this context substantially surrounds a portion of the anchor blade is meant to convey that the relevant blade sleeve tunnel has a series of cross sections taken perpendicular to a midline of the blade sleeve tunnel and a majority of the series of cross sections are solid so that at that cross section of the blade sleeve tunnel, the anchor blade is totally surrounded by that cross section of the blade sleeve tunnel. This feature allows significant force to be applied to the anchor blades as may be required to drive the tips of the anchor blades through the cortical bone on the relevant vertebra.

Another way to summarize some of the teachings for the present disclosure is a fusion implant with a cephalad anchor blade and a caudal anchor blade held within the fusion implant in a delivery position before removal from sterilized packaging. The fusion implant having an implant body, a cephalad anchor blade for extending into a cephalad vertebra after the fusion implant is delivered between the cephalad vertebra and a caudal vertebra, and a caudal anchor blade for extending into the caudal vertebra after the fusion implant is delivered between the cephalad vertebra and the caudal vertebra.

The cephalad anchor blade having a cephalad proximal end having a cephalad lock plane for use in locking the cephalad anchor blade in a deployed position, and a cephalad stop plane facing distally which prevents the cephalad proximal end from traveling beyond a proximal face of the implant body into an interior of the implant body.

The caudal anchor blade having a caudal proximal end having a caudal lock plane for use in locking the caudal anchor blade in a deployed position; and a caudal stop plane facing distally which prevents the caudal proximal end of the caudal anchor blade from traveling beyond the proximal face of the implant body into the interior of the implant body.

The fusion implant having a set of at least one locking cam rotatably engaged with the implant body wherein each of the set of at least one locking cam has a delivery position wherein each the set of at least one locking cam does not limit:

movement of the cephalad anchor blade; or movement of the caudal anchor blade.

Each of the set of at least one locking cam also having a locking position wherein:

the cephalad anchor blade that is in the deployed position cannot move the cephalad proximal end in a proximal direction away from the proximal face of the implant body; and the caudal anchor blade that is in the deployed position cannot move the caudal proximal end in a proximal direction away from the proximal face of the implant body.

More specifically, a cephalad locking cam once moved into the locking position traps a cephalad locking plane of the cephalad anchor blade so that the cephalad anchor blade is limited in ability for distal movement beyond the proximal face of the fusion implant by the cephalad stop plane and is limited in ability for further proximal movement by the cephalad locking cam contacting the cephalad locking plane.

And a caudal locking cam in the locking position traps a caudal locking plane of the caudal anchor blade so that the caudal anchor blade is limited for further distal movement beyond the proximal face of the fusion implant by the caudal stop plane and is limited for further proximal movement by the caudal locking cam contacting the caudal locking plane.

Some of the teachings of the present disclosure may be summarized as a process to deploy a fusion implant with anchor blades and then lock the anchor blades in a deployed position. More specifically, opening a container and removing a fusion implant which already has a cephalad anchor blade and a caudal anchor blade which are both held in a non-deployed position for delivery between a cephalad vertebra and a caudal vertebra.

Positioning the fusion implant between the cephalad vertebra and the caudal vertebra while the cephalad anchor blade and the caudal anchor blade are both held in the non-deployed position. Advancing the cephalad anchor blade into a deployed position which engages the cephalad vertebra and advancing the caudal anchor blade into a deployed position which engages the caudal vertebra.

Using a cephalad locking cam to lock the cephalad anchor blade in the deployed position; and using a caudal locking cam to lock the caudal anchor blade in the deployed position.

Other systems, methods, features and advantages of the disclosed teachings will be immediately apparent or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

FIG. 3 shows a perspective view of a fusion implant 100 having an implant body 200.

FIG. 4 shows a similar perspective view of the same fusion implant 100 but in the deployed position with a distal tip 304 of the cephalad anchor blade 300 fully extended beyond the cephalad face 130 of the fusion implant 100.

FIG. 13 shows the fusion implant 100 in the delivery position with the distal tip 354 of the caudal anchor blade 350 recessed within the caudal blade sleeve tunnel 254.

FIG. 14 shows caudal face 140 of the fusion implant 100 while the caudal anchor blade 350 and the cephalad anchor blade 300 are in the deployed position.

FIG. 19 is a view of the cephalad face 130 of the fusion implant 100 in the delivery position with the implant body 200 rendered invisible.

FIG. 20 is a view of the cephalad face 130 of the fusion implant 100 in the deployed position with the implant body 200 rendered invisible.

FIG. 25 is a flowchart for a process 1000 to deploy a fusion implant with pre-assembled anchor blades and then lock the anchor blades in a deployed position.

DETAILED DESCRIPTION

Figure 1:
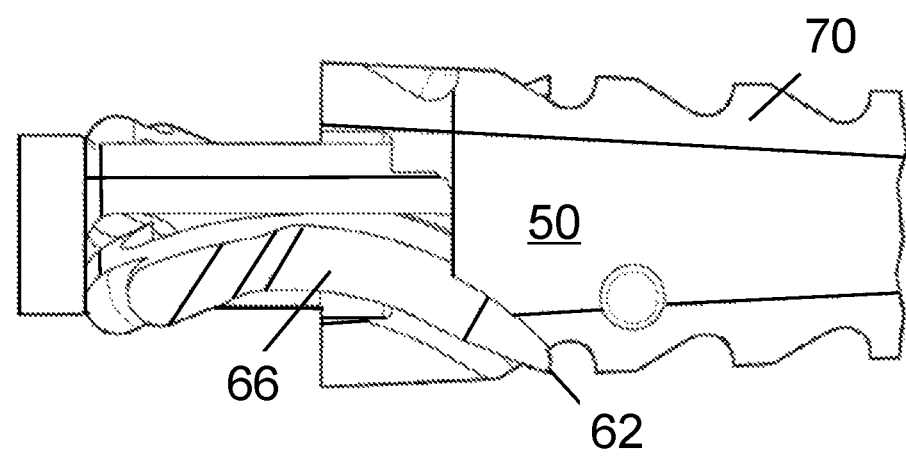
FIG. 1 is a prior art spinal implant 50 suitable for use in spinal fusion with the distal tip 54 of the cephalad anchor blade 58 and the distal tip 62 of the caudal anchor blade 66 both in a retracted position.
Figure 2:
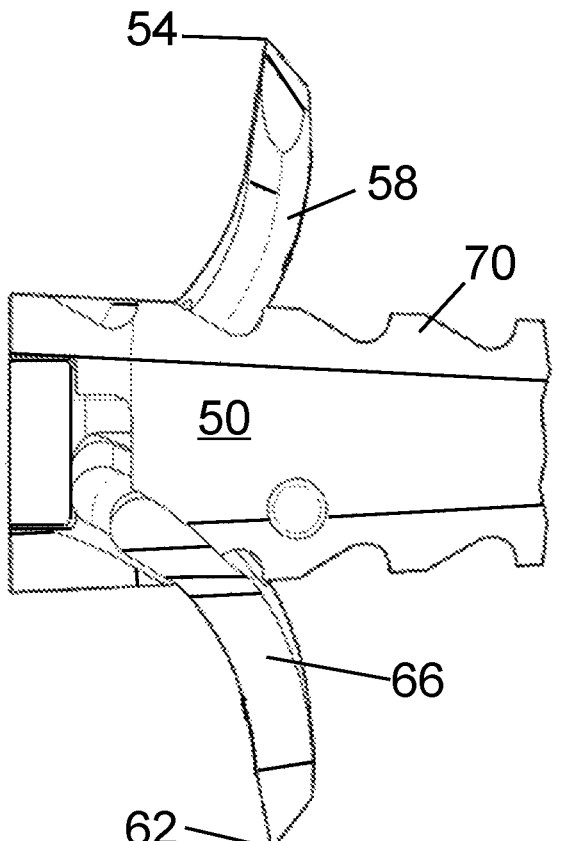
FIG. 2 shows the prior art spinal implant 50 of FIG. 1 after delivery into the intervertebral space and deployment of the cephalad anchor blade 58 and caudal anchor blade 66 through the cortical bone endplates of the adjacent vertebrae.

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies.

Figures 3, 4:
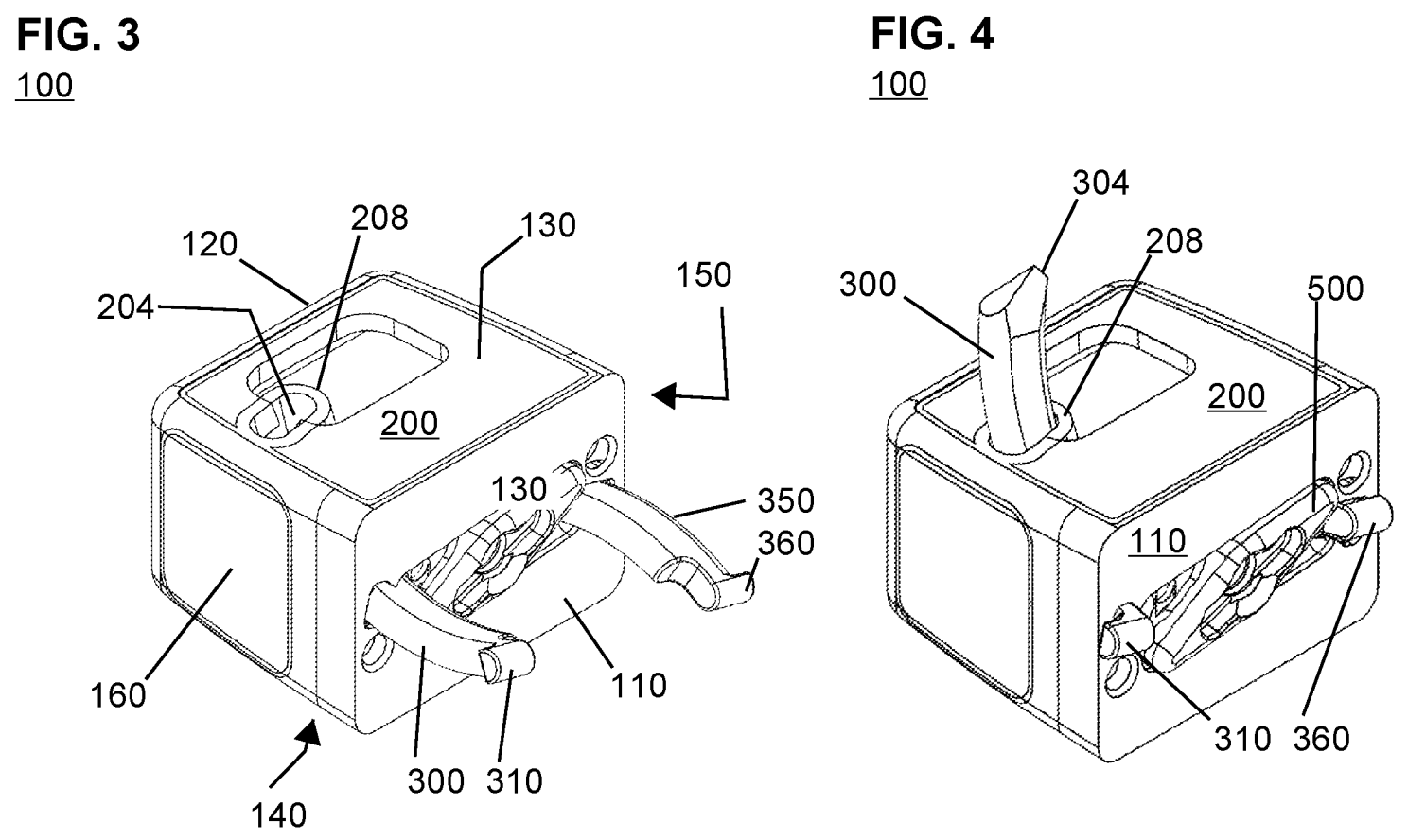

FIG. 3 shows a perspective view of a fusion implant 100 having an implant body 200. The implant body 100 has a proximal face 110 which is opposite a distal face 120. The distal face 120 is intended to be the leading face of the fusion implant 100 during insertion into a patient's intervertebral space. To the right of the proximal face 110 is the right face 150. Opposite the right face 150 is the left face 160.

FIG. 3 shows the fusion implant in the delivery position with the cephalad anchor blade 300 and the caudal anchor blade 350 extending from the proximal face 110 and not extending from either the cephalad face 130 or the caudal face 140. The stop arm 310 on the cephalad anchor blade 300 and the stop arm 360 on the caudal anchor blade 350 are both away from the proximal face 110 of the implant body 200.

FIG. 4 shows a similar perspective view of the same fusion implant 100 but in the deployed position with a distal tip 304 of the cephalad anchor blade 300 fully extended beyond the cephalad face 130 of the fusion implant 100. Caudal anchor blade 350 is also fully extended although the distal tip 354 of the caudal anchor blade 350 is not visible in this view. The stop arm 310 on the cephalad anchor blade 300 and the stop arm 360 on the caudal anchor blade 350 are resting in proximity to the proximal face 110 of the implant body 200 after limiting the travel of the anchor blades (300 and 350) relative to the implant body 200.

Note that a portion of the cephalad blade sleeve tunnel 204 (FIG. 3) is visible including the cephalad sleeve tunnel egress opening 208 that totally encircles the cephalad anchor blade 300.

One of skill in the art will discern that the cephalad blade sleeve tunnel has a series of cross sections which may be taken perpendicular to a midline of the cephalad blade sleeve tunnel and the majority of the series of cross sections are solid so that at that cross section of the cephalad blade sleeve tunnel, the cephalad blade anchor is totally surrounded by that cross section of the cephalad blade sleeve tunnel.

Likewise, one of skill in the art will discern that the caudal blade sleeve tunnel has a series of cross sections which may be taken perpendicular to a midline of the caudal blade sleeve tunnel and the majority of the series of cross sections are solid so that at that cross section of the caudal blade sleeve tunnel, the caudal blade anchor is totally surrounded by that cross section of the caudal blade sleeve tunnel.

Also visible in FIG. 4 is the proximal side of the locking cam 500 which is shown in the unlocked position. Unlocked means that the locking cam 500 is not in position to resist the movement of the cephalad anchor blade 300 or the caudal anchor blade 350 from movement from the deployed position shown in FIG. 4 to the delivery position shown in FIG. 3.

Figures 5, 6:
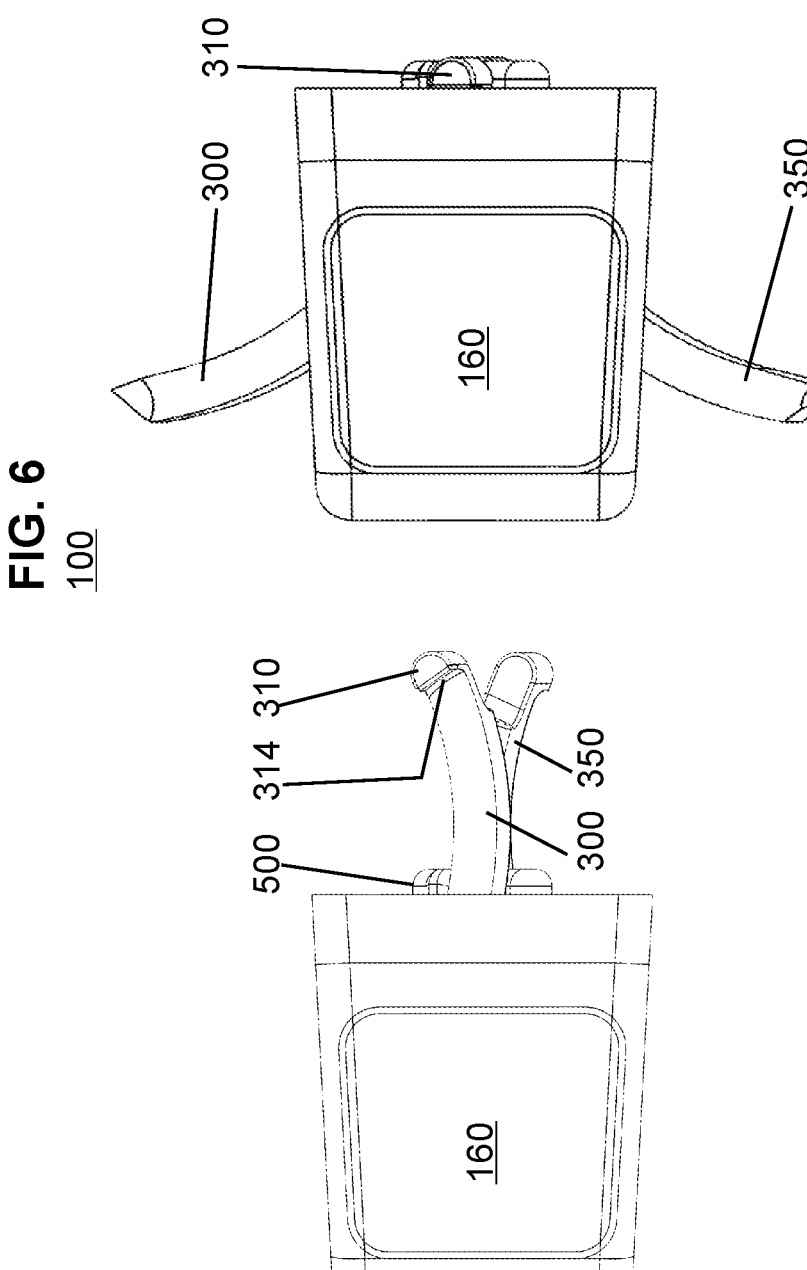
FIG. 5 shows the left face 160 of the fusion implant 100 in the delivery position.
FIG. 6 shows the left face 160 of the fusion implant 100 in the deployed position with cephalad anchor blade 300 and caudal anchor blade 350 in the deployed position.

FIG. 5 shows the left face 160 of the fusion implant 100 in the delivery position. Stop plane 314 on stop arm 310 of the cephalad anchor blade can be seen in FIG. 5.

FIG. 6 shows the left face 160 of the fusion implant 100 in the deployed position with cephalad anchor blade 300 and caudal anchor blade 350 in the deployed position.

Figures 7, 8:
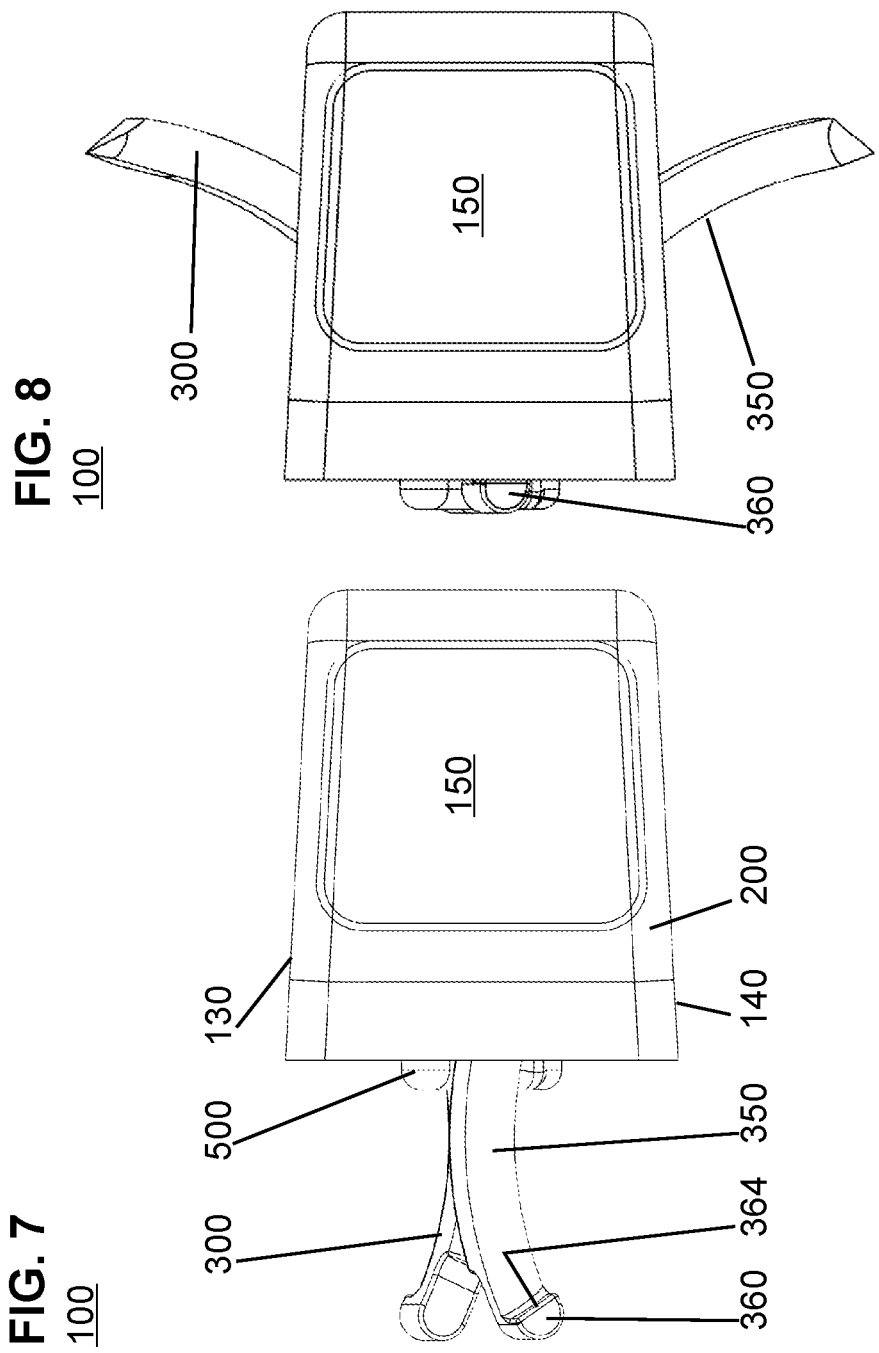
FIG. 7 shows the right face 150 of the fusion implant 100 in the delivery position. Stop plane 364 on stop arm 360 can be seen in FIG. 7.
FIG. 8 shows the right face 150 of the fusion implant 100 in the deployed position with cephalad anchor blade 300 and caudal anchor blade 350 in the deployed position.

FIG. 7 shows the right face 150 of the fusion implant 100 in the delivery position. Stop plane 364 on stop arm 360 can be seen in FIG. 7. Cephalad face 130 is not parallel with caudal face 140 of the implant body 200.

FIG. 8 shows the right face 150 of the fusion implant 100 in the deployed position with cephalad anchor blade 300 and caudal anchor blade 350 in the deployed position.

Figures 9, 10:
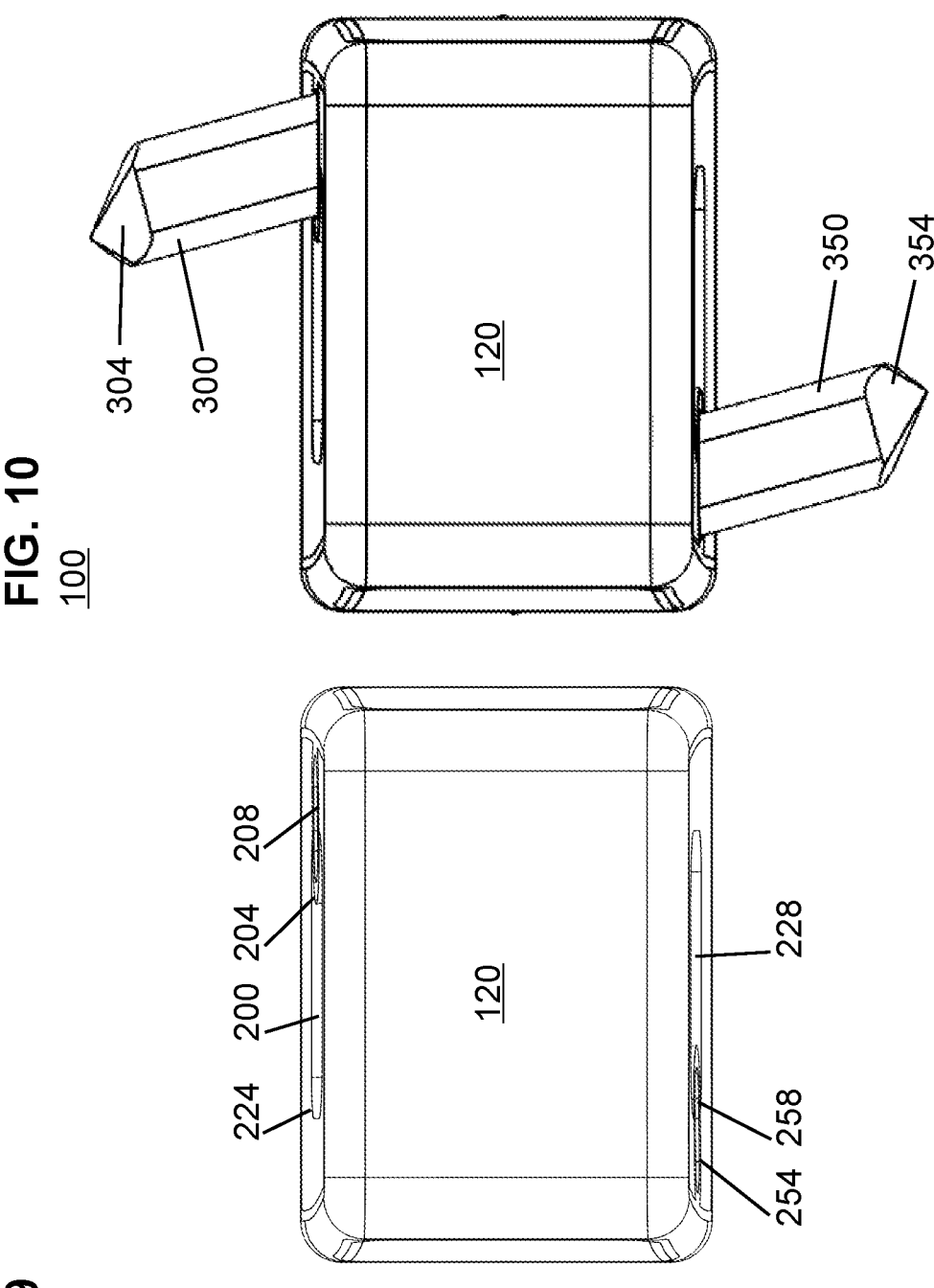
FIG. 9 shows the distal face 120 of the fusion implant 100 while in the delivery position.
FIG. 10 shows the distal face 120 of the fusion implant 100 while in the deployed position with cephalad anchor blade 300 and caudal anchor blade 350 in the deployed positions.

FIG. 9 shows the distal face 120 of the fusion implant 100 while in the delivery position. As this instance of the implant body 200 tapers from the proximal face 110 to the distal face 120, FIG. 9 includes:

The cephalad sleeve tunnel egress opening 208 at the end of the cephalad blade sleeve tunnel 204.

The caudal sleeve tunnel egress opening 258 at the end of the caudal blade sleeve tunnel 254.

The cephalad open end 224 of the bone growth conduit 220.

The caudal open end 228 of the bone growth conduit 220.

A bone growth conduit 220 extending from the cephalad face 130 to the caudal face 140 of a fusion implant 100 may be used to allow bone growth to connect the adjacent vertebrae endplates through the interior of the fusion implant 100. Those of skill in the art understand that the fusion implant 100 may be packed with bone or other material to facilitate this bone growth.

FIG. 10 shows the distal face 120 of the fusion implant 100 while in the deployed position with cephalad anchor blade 300 and caudal anchor blade 350 in the deployed positions. The cross sections of the cephalad blade sleeve tunnel 204 and the caudal blade sleeve tunnel 254 may closely approximate the outer perimeter of the intermediate portions of the cephalad anchor blade 300 and the caudal anchor blade 350 so as to constrain and provide guidance to the movement of the anchor blades (300 and 350) while the distal tips (304 and 354) penetrate the cortical bone vertebral endplates and proceed into the vertebrae.

Figure 11:
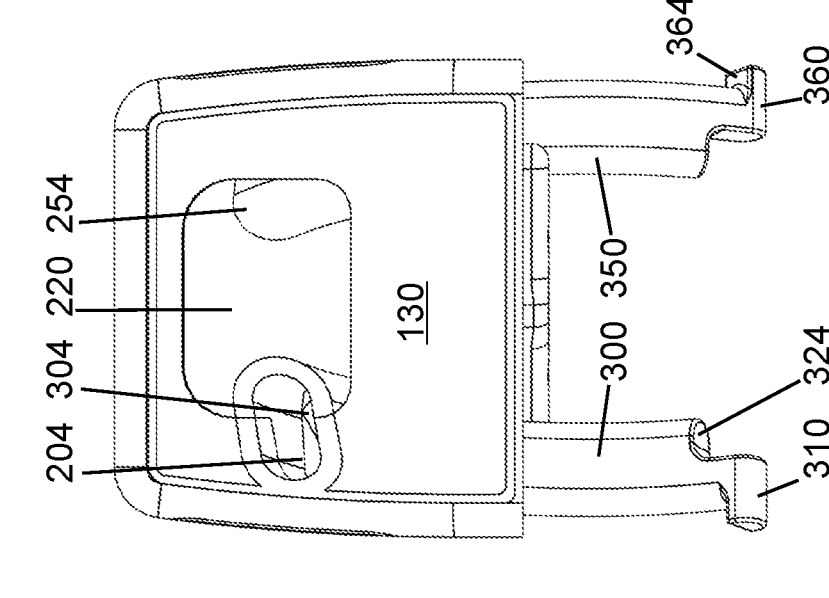
FIG. 11 shows the cephalad face 130 of the fusion implant 100 including bone growth conduit 220 and the distal tip 304 of the cephalad anchor blade 300 within the cephalad blade sleeve tunnel 204.

FIG. 11 shows the cephalad face 130 of the fusion implant 100 including bone growth conduit 220 and the distal tip 304 of the cephalad anchor blade 300 within the cephalad blade sleeve tunnel 204. A portion of the caudal blade sleeve tunnel 254 may be viewed through the bone growth conduit 220. A lock plane 324 of the cephalad anchor blade 300 may be locked in place by the locking cam 500 as discussed below.

Stop plane 364 on stop arm 360 of caudal anchor blade 350 limits the travel of the caudal anchor blade 350 through the caudal blade sleeve tunnel 254.

Figure 12:
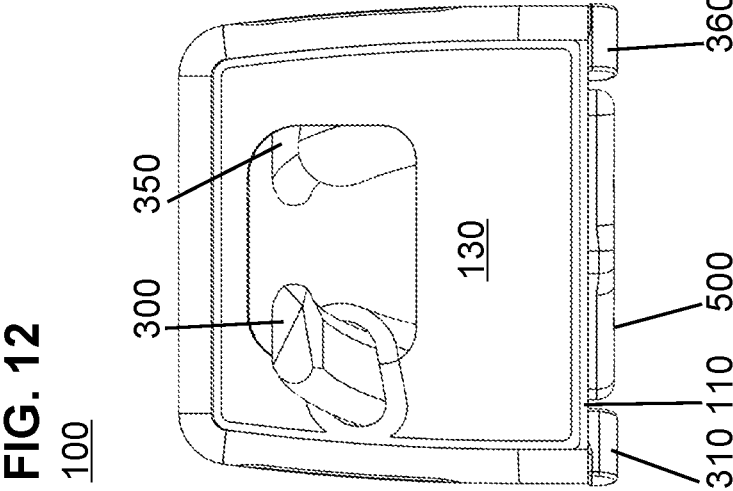
FIG. 12 shows the cephalad face 130 of the fusion implant 100 in the deployed position with cephalad anchor blade 300 and caudal anchor blade 350 in the deployed position and stop arms 310 and 360 adjacent the proximal face 110 of the fusion implant 100.

FIG. 12 shows the cephalad face 130 of the fusion implant 100 in the deployed position with cephalad anchor blade 300 and caudal anchor blade 350 in the deployed position and stop arms 310 and 360 adjacent the proximal face 110 of the fusion implant 100.

Figures 13, 14:
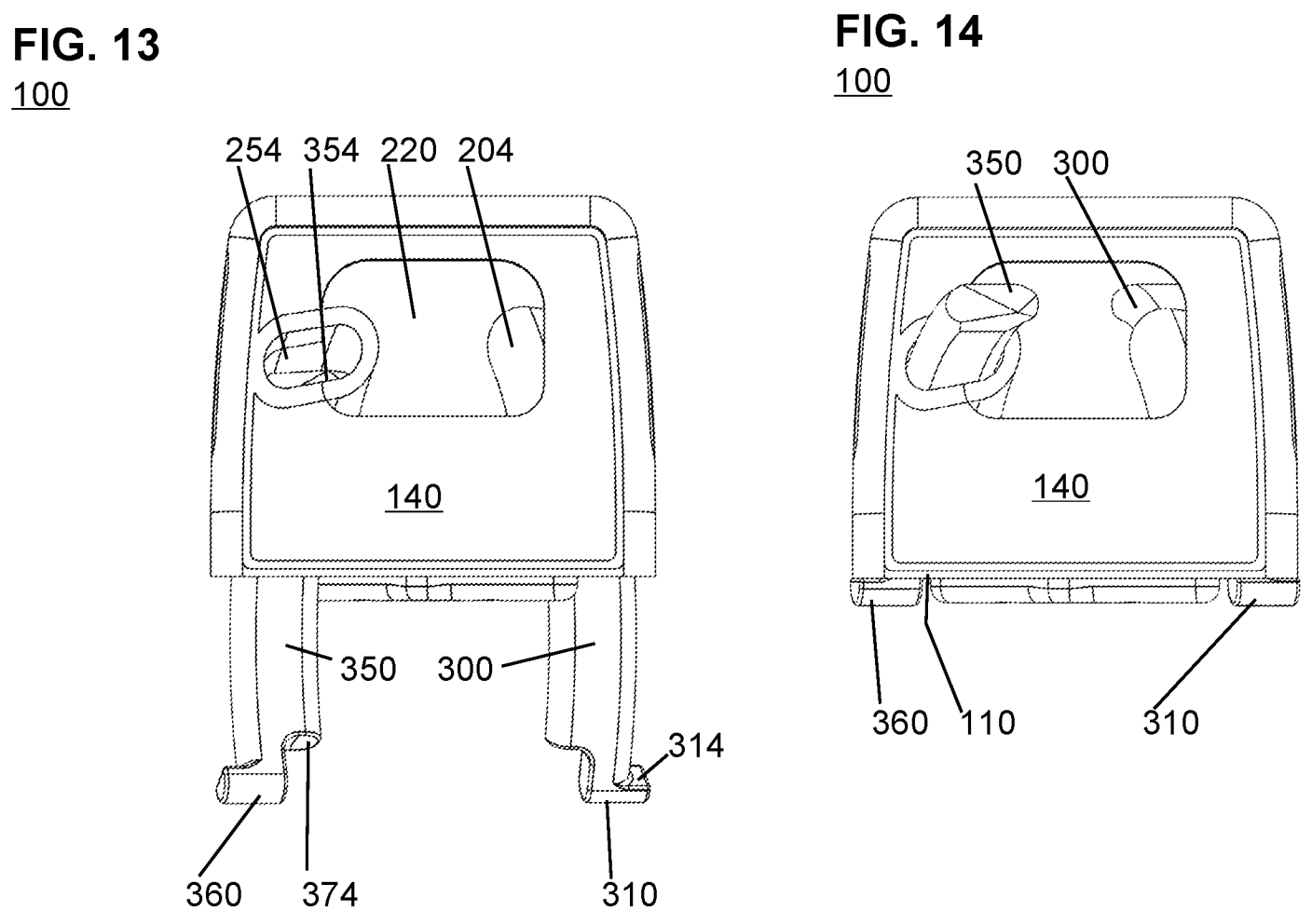

FIG. 13 and FIG. 14 for this instance of a fusion implant 100 are mirror images of FIG. 11 and FIG. 12. FIG. 13 shows the fusion implant 100 in the delivery position with the distal tip 354 of the caudal anchor blade 350 recessed within the caudal blade sleeve tunnel 254. The cephalad blade sleeve tunnel 204 is visible through the bone growth conduit 220. The lock plane 374 of the caudal anchor blade 350 may be held by the locking cam 500 to hold the caudal anchor blade 350 in the deployed position. FIG. 13 shows the stop plane 314 of the cephalad anchor blade 300.

FIG. 14 shows caudal face 140 of the fusion implant 100 while the caudal anchor blade 350 and the cephalad anchor blade 300 are in the deployed position. Stop arms 360 and 310 are adjacent to the proximal face 110 of the fusion implant 100 and ready to be locked in place by the locking cam 500.

Figure 15:
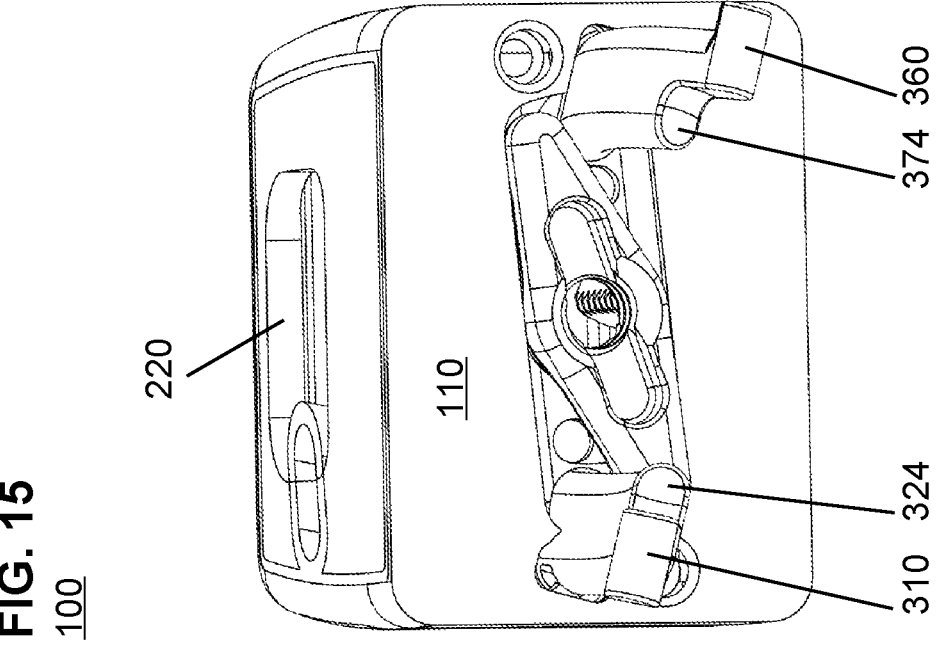
FIG. 15 shows a perspective view of the proximal face 110 and the cephalad face 130 of the fusion implant 100 in the delivery position with stop arms 310 and 360 away from the proximal face 110 of the fusion implant. Both lock planes 324 and 374 are visible as is a portion of the bone growth conduit 220.

FIG. 15 shows a perspective view of the proximal face 110 and the cephalad face 130 of the fusion implant 100 in the delivery position with stop arms 310 and 360 away from the proximal face 110 of the fusion implant. Both lock planes 324 and 374 are visible as is a portion of the bone growth conduit 220. FIG. 15 shows the same view as FIG. 16 but with the cephalad anchor blade 300 and the caudal anchor blade 350 in the deployed position with the stop arms 310 and 360 adjacent to the proximal face 110 and the lock planes 324 and 374 ready for retention by the locking cam 500.

Figure 16:
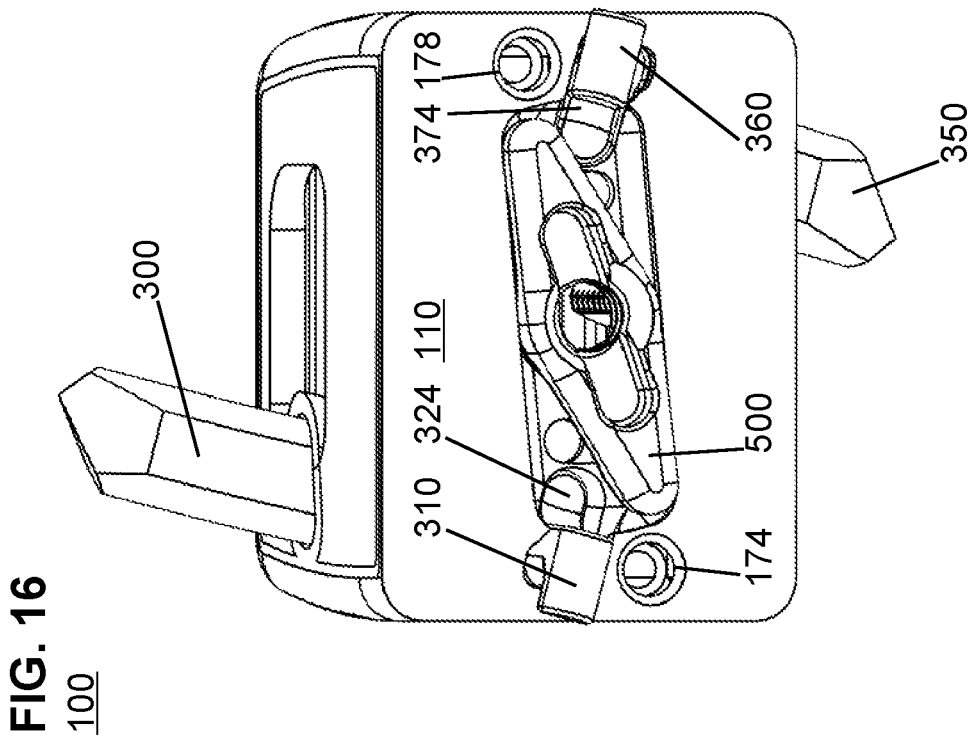
FIG. 16 shows the first tool bore 174 and second tool bore 178 for engagement by the delivery tooling.

FIG. 16 shows the first tool bore 174 and second tool bore 178 for engagement by the delivery tooling.

Figures 17, 18:
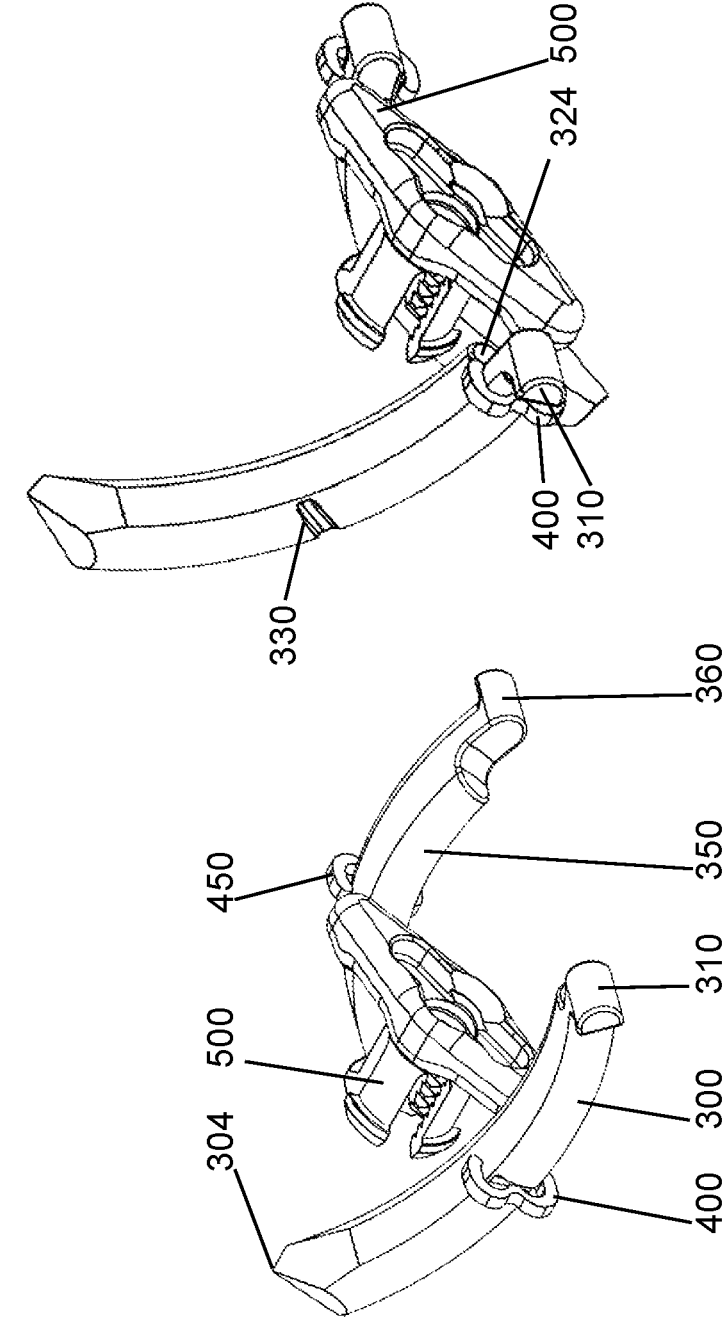
FIG. 17 is a view similar to the view in FIG. 3 of the fusion implant 100 shown in a perspective that shows the cephalad face 130, left face 160, and proximal face 110.
FIG. 18 is a view similar to FIG. 4 and like FIG. 17 has the implant body 200 rendered invisible to expose the retention clips 400 and 450.

FIG. 17 is a view similar to the view in FIG. 3 of the fusion implant 100 shown in a perspective that shows the cephalad face 130, left face 160, and proximal face 110. To reveal the retention clips 400 and 450, the implant body 200 has been made invisible. From this view, the cephalad retention clip 400 is engaged with the cephalad anchor blade 300 and the caudal retention clip 450 is engaged with the caudal anchor blade 350. Thus while the fusion implant 100 is in the delivery position, including while being delivered to the intervertebral space, the engaged anchor blades 300 and 350 are immobile within the fusion implant 100 as they are retained in a fixed position by the engaged retention clips 400 and 450.

FIG. 18 is a view similar to FIG. 4 and like FIG. 17 has the implant body 200 rendered invisible to expose the retention clips 400 and 450. The retention groove 330 on the cephalad anchor blade 300 is no longer engaged by the retention clip 400 to hold the cephalad anchor blade 300 in a fixed position during delivery of the fusion implant 100. The retention clip 400 bends out of the way as the cephalad anchor blade 300 is urged towards the deployed position after delivery. The retention clip 400 is not engaged with the cephalad anchor blade 300 when in the deployed position as retention of the cephalad anchor blade 300 in the deployed position is achieved by rotation of the locking cam 500 to engage the lock plane 324. The locking cam 500 as shown in FIG. 18 is not yet in the locked position and thus, lock plane 324 is not covered by the locking cam 500.

Those of skill in the art will be able to adapt the teaching of an anchor blade retention clip to use a different shape of retention clip or to engage a different portion of the anchor blade. This teaching is not limited to engagement with the portion of the anchor blade closest to the left face or right face of the fusion implant. Likewise, one could position the retention clips close to the sleeve tunnel egress openings 208 and 258.

Figures 19, 20:
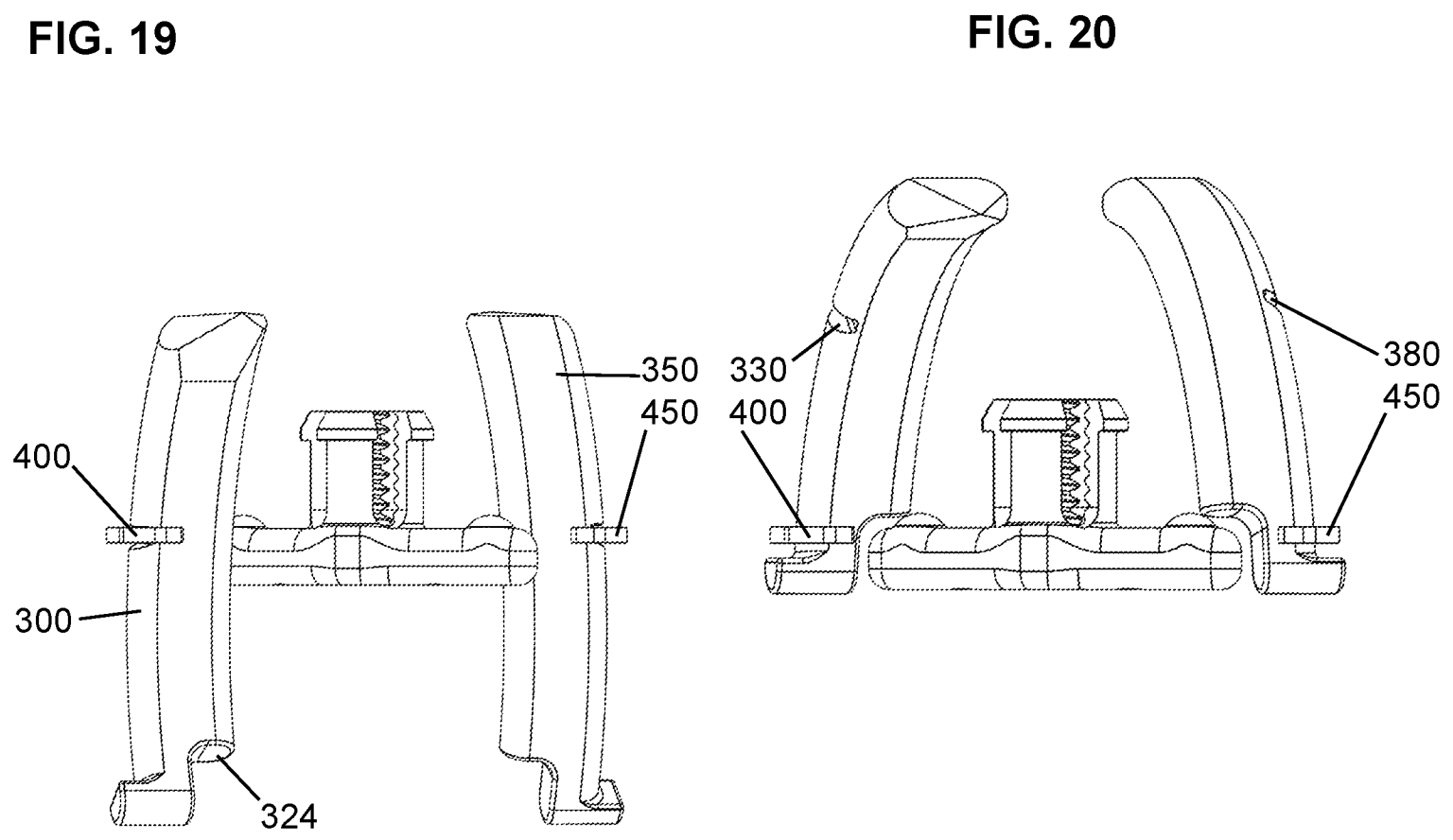

FIG. 19 is a view of the cephalad face 130 of the fusion implant 100 in the delivery position with the implant body 200 rendered invisible. Cephalad retention clip 400 is retaining the cephalad anchor blade 300 in the delivery position. Caudal retention clip 450 is retaining caudal anchor blade 350 in the delivery position.

FIG. 20 is a view of the cephalad face 130 of the fusion implant 100 in the deployed position with the implant body 200 rendered invisible. Cephalad retention clip 400 is no longer retaining the cephalad anchor blade 300 in the delivery position. Retention groove 330 is no longer engaged with cephalad retention clip 400. Caudal retention clip 450 is no longer retaining caudal anchor blade 350 in the delivery position. Retention groove 380 is no longer engaged with caudal retention clip 450.

Locking Cam.

Figures 21, 22, 23:
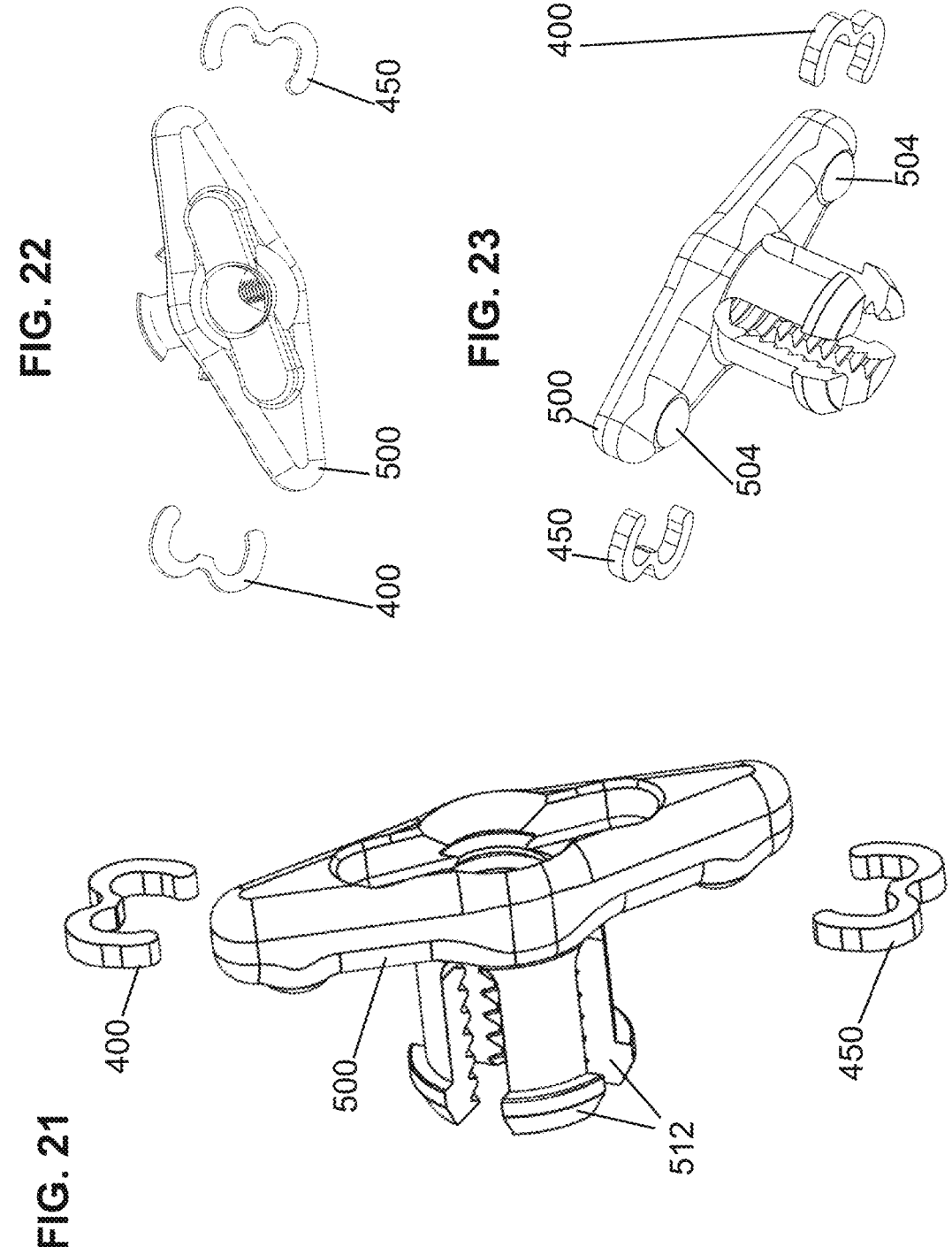
FIG. 21, FIG. 22, and FIG. 23 show additional views of the fusion implant 100 with the implant body 200 and both anchor blades (300 and 350) rendered invisible.

FIG. 21, FIG. 22, and FIG. 23 show additional views of the fusion implant 100 with the implant body 200 and both anchor blades (300 and 350) rendered invisible. These views show additional details for the cephalad retention clip 400, the caudal retention clip 450, and the locking cam 500. As seen in FIG. 23, locking cam 500 has engagement domes 504 on the cam arms 508 that can engage with portions of the proximal face 110 of the implant body 200 to retain the locking cam 500 in the unlocked position or in a locked position that covers the lock planes 324 and 374 to hold the cephalad anchor blade 300 and the caudal anchor blade 350 in the deployed position.

The surgeon receives three different types of feedback when the locking cam 500 is moved into position. As the locking cam 500 is moved, the cam arms 508 bend outward and both the engagement domes 504 and the proximal face 110 of the fusion implant 100 deform to some extent. The surgeon receives a visual indication, an audible indication, and a haptic indication when the locking cam 500 is moved into position as the bent cam arms 508 drive the engagement domes 504 into the ball detents in the proximal face 110 of the fusion implant 100 (discussed below).

One of skill in the art will appreciate that the four distal prongs 512 on the locking cam 500 allow for the locking cam 500 to be added to the implant body 200 while retaining the ability to rotate the locking cam 500.

Figure 24:
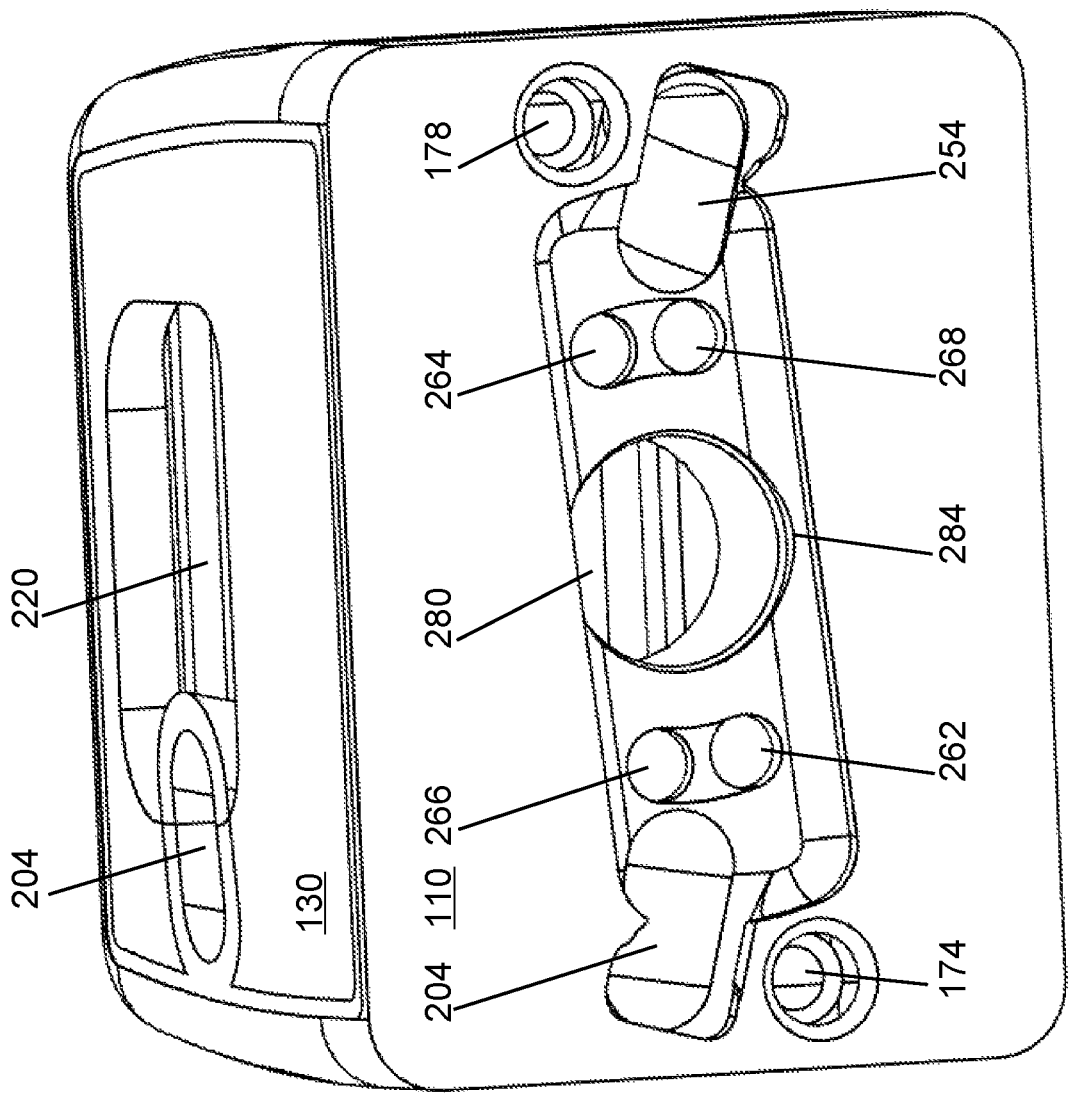
FIG. 24 shows a perspective view of the implant body 200 showing the cephalad face 130 and the proximal face 110.

FIG. 24 shows a perspective view of the implant body 200 showing the cephalad face 130 and the proximal face 110. A number of previously introduced elements are visible in FIG. 24 including:

First tool bore 174
    Second tool bore 178
    Cephalad blade sleeve tunnel 204
    Caudal blade sleeve tunnel 254
    Bone growth conduit 220

FIG. 24 also shows locking cam bore 280 and bore end 284. Ball detent 262 and ball detent 264 hold the engagement domes 504 of the locking cam 500 when the locking cam 500 is in the unlocked position. Ball detent 266 and ball detent 268 hold the engagement domes 504 of the locking cam 500 when the locking cam 500 is in the locked position limiting the movement of lock planes 324 and 374 on anchor blades 300 and 350.

Method of Use.

FIG. 25 is a flowchart for a process 1000 to deploy a fusion implant with pre-assembled anchor blades and then lock the anchor blades in a deployed position. Note, the steps for creating access to the disc space, distraction, discectomy, endplate preparation, and implant size selection may be done in conventional ways and need not be described here.

Step 1004—Open a container having a pre-assembled fusion implant 100 with a cephalad anchor blade 300 held in a delivery position by a cephalad retention clip 400 and a caudal anchor blade 350 held in a delivery position by a caudal retention clip 450. With a locking cam 500 on the fusion implant 100 that is not yet in a locked position. As noted below, the retention clips could be replaced with the use of interference fits. The form of the container is not critical but it is expected that the anchor blades anchor blades (300 and 350) are held in a delivery position within the fusion implant 100 before the final packaging and sterilization of the fusion implant.

Step 1008—Position the fusion implant 100 between two adjacent vertebrae: a cephalad vertebra and an adjacent caudal vertebra. This may be done using one or more tools for implant delivery. The implant tool may have a depth stop to limit the depth of insertion of the implant into the intervertebral disc space. Proper positioning may be confirmed by radiographic imaging as is known in the art.

Step 1012—Advance the cephalad anchor blade 300 causing release of the cephalad retention clip 400 and move the cephalad anchor blade 300 into a deployed position that is engaged with the cephalad vertebra and advance the caudal anchor blade 350 causing release of the caudal retention clip 450 and move the caudal anchor blade 350 into a deployed position that is engaged with the caudal vertebra. Those of skill in the art will appreciate that moving the distal tips of the anchor blade through cortical bone will require substantial force and may require the use of a mallet to provide impacts that urge the distal tips of the anchor blade through the cortical bone into the softer cancellous bone. A preferred mode is simultaneous advancement of the distal tips of both anchor blades through the use of mallet impacts. But one of skill in the art will appreciate that the fusion implant 100 described in this disclosure could be used in a process that does not simultaneously advance both anchor blades.

Step 1016—Rotate the locking cam 500 to the locked position such that the locking cam traps the cephalad anchor blade 300 between the locking cam 500 and the proximal face 110 of the implant body 200 and the locking cam traps the caudal anchor blade 350 between the locking cam 500 and the proximal face 110 of the implant body 200 so that the anchor blades are trapped in their deployed position until the locking cam is move from the locked position.

Note that in step 1016, ideally the locking cam 500 engages with the proximal face 110 of the implant body 200 to resist movement of the locking cam 500 from the locked position. The present disclosure used engagement domes 504 on the distal face of the cam arms 508 of the locking cam 500 to engage with ball detent 266 and ball detent 268 on the proximal face 110 of the implant body 200. Those of skill in the art can envision other ways to lock the rotational position of the locking cam 500 with respect to the proximal face 110 of the implant body 200.

Advantages

A Preassembled Fusion Implant.

The use of retention clips (400 and 450) to hold preloaded anchor blades (300 and 350) within a fusion implant 100 is an advantage over earlier bladed fusion implants that had anchor blades that were loaded into the implant body as the implant body was being loaded into a delivery tool. One advantage is an elimination of a possible source of error. Having the anchor blades (300 and 350) already retained in proper delivery position avoids any chance for error or delay. It is expected that the anchor blades anchor blades (300 and 350) are held in a delivery position within the fusion implant 100 before the final packaging and sterilization of the fusion implant.

Any reduction in the need to handle blades by operating room staff is a desirable modification. Here the distal tips (304 and 354) intended to pierce cortical bone are safely recessed within the blade sleeve tunnels (204 and 254) and thus provide no risk to the operating room staff. The pre-loaded fusion implant 100 may simply be removed from the sterile packaging and is ready for delivery.

Note, a fusion implant otherwise using one or more teachings of the present disclosure is not excluded from the scope of the disclosure if the anchor blades are held in a pre-deployed position having the distal tips (304 and 354) intended to pierce cortical bone less that fully safely recessed within the blade sleeve tunnels (204 and 254). Those of skill in the art recognize that such an implant device may still be delivered between the cephalad vertebra and the caudal vertebra as the pair of vertebrae may be temporarily distracted beyond the required size and some scoring of the vertebrae endplates is tolerable as abrasion of the endplates is a normal part of the fusion preparation in order to facilitate vascularization between the endplate and the bone graft material used in the fusion process.

Alternatives and Variations

Implant Body Shapes.

Those of skill in the art appreciate that implant bodies are frequently provided in a range of sizes for use with different sized patients and at different intervertebral gaps in the human spine. Further, the surgeon is frequently offered a choice between having a cephalad face that is substantially parallel to the caudal face, the cephalad face and caudal faces not parallel (as in lordotic implants), or the cephalad face curved or domed.

Figure 26:
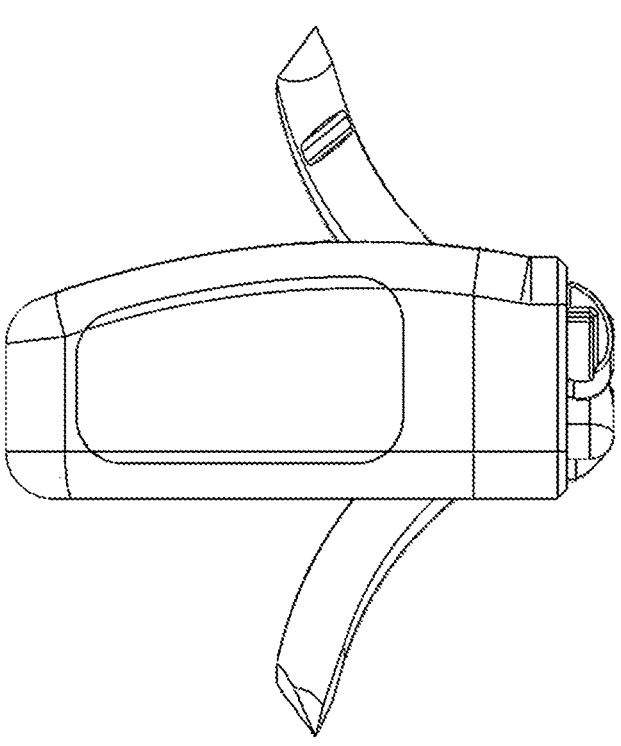
FIG. 26 shows a fusion implant 904 that is known as a convex implant.
Figure 27:
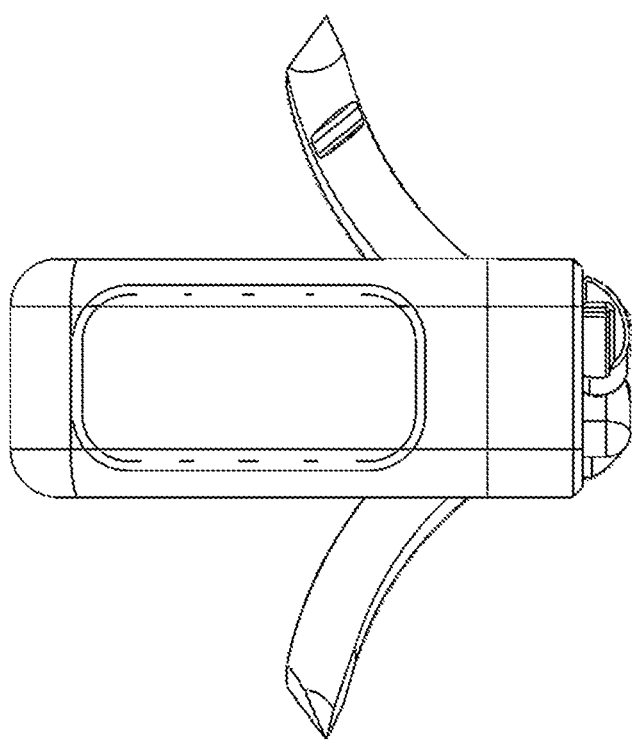
FIG. 27 shows a fusion implant 908 that is a parallel implant.

Those of skill in the art will recognize from at least FIG. 5 through FIG. 8, that these figures show a fusion implant 100 as a lordotic implant based upon the slopes of the cephalad face 130 and the caudal face 140. The teachings of the present disclosure may be used with different fusion implants having a pair of the cephalad face 130 and the caudal face 140 that is different from fusion implant 100. For example, FIG. 26 shows a fusion implant 904 that is known as a convex implant. FIG. 27 shows a fusion implant 908 that is a parallel implant. Those of skill in the art will be able to take the teachings of the present disclosure and adapt the fusion implant components for scale and body shape choices beyond the few examples shown in this disclosure.

Implant Body Fabrication.

Implant body fabrication may be done in a variety of ways while staying within the scope of the teachings of the present application. Most likely the implant body fabrication will be performed using an additive manufacturing technique. One viable way to make implant bodies as taught in this application is to use Electron Beam Melting (EBM) technology. (See www.ge.com/additive/ebm)

The implant body can be additively manufactured from a titanium alloy (Ti-6Al-4V ELI), per ASTM F3001 a material with known biocompatibility. This titanium alloy promotes bony ingrowth, providing fusion of the cervical spine. In addition to the titanium alloy structure, the cage utilizes ChoiceSpine's proprietary BioBond™ endplates which feature an organic lattice structure that provides an osteoconductive surface for bony ingrowth. Thanks to additive manufacturing, the implant body can be created with continuous porosity from endplate to endplate, allowing fusion of the cervical spine both to and through the cage rather than dead-ending at the endplates. The ability to promote bony ingrowth to and through the implant body makes this material desirable. Taken from https://choicespine.com/creating-a-superior-cervical-cage-tiger-shark-c/(space added to avoid live link).

Manufacturing of the Anchor Blades

Those of skill in the art will appreciate that the geometries of the anchor blades afford the option of traditional manufacturing methods. The preferred material for anchor blades is titanium such as titanium alloy (Ti-6Al-4V ELI) anchors per ASTM F136. Additive manufacturing methods may be used but are not required.

Differences between Anchor Blades.

Those of skill in the art will appreciate that economies may be obtained by having one anchor blade design that may be used as either the cephalad anchor blade 300 or the caudal anchor blade 350. However, the teachings of the present disclosure do not require interchangeable anchor blade arms. Likewise, there is a preference for using one part number for the cephalad retention clip 400 and the caudal retention clip 450 but this is not required. The interaction between the cephalad retention clip 400 and the retention groove 330 on the cephalad anchor blade 300 may be different from the interaction with the caudal retention clip 450 and the retention groove 380 on the caudal anchor blade 350.

Retention Clips Material.

Figure 28:
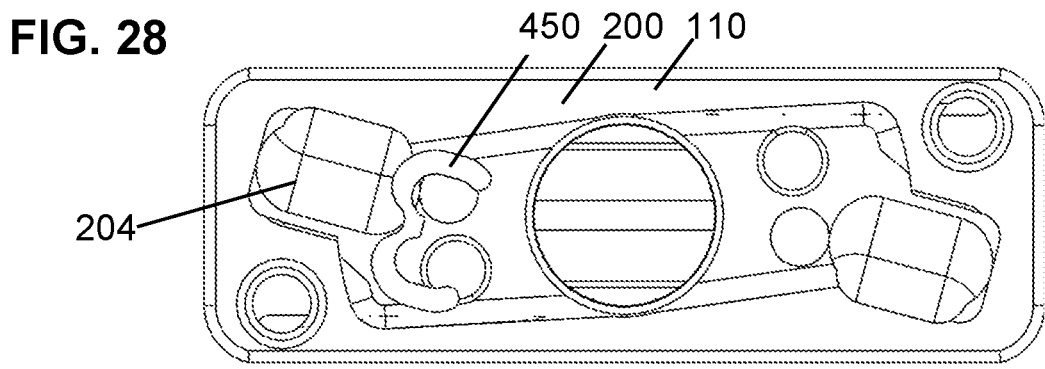
FIG. 28, FIG. 29, and FIG. 30 show a sequence of steps for inserting the cephalad retention clip into the implant body.
Figure 29:
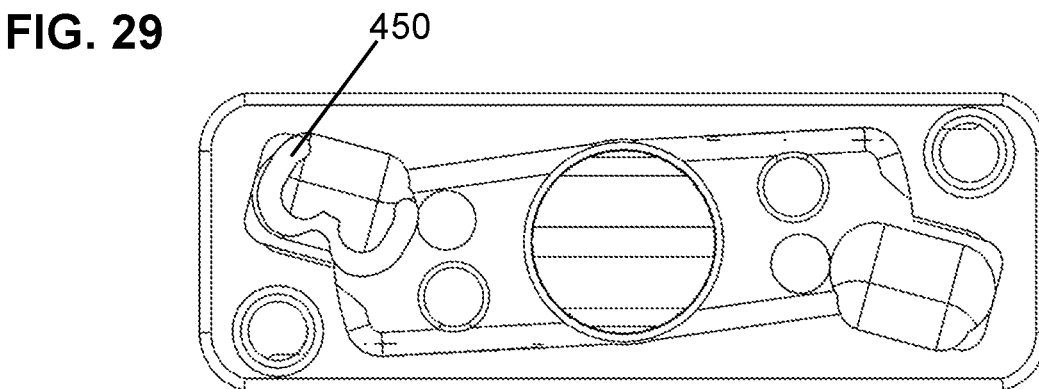
Figure 30:
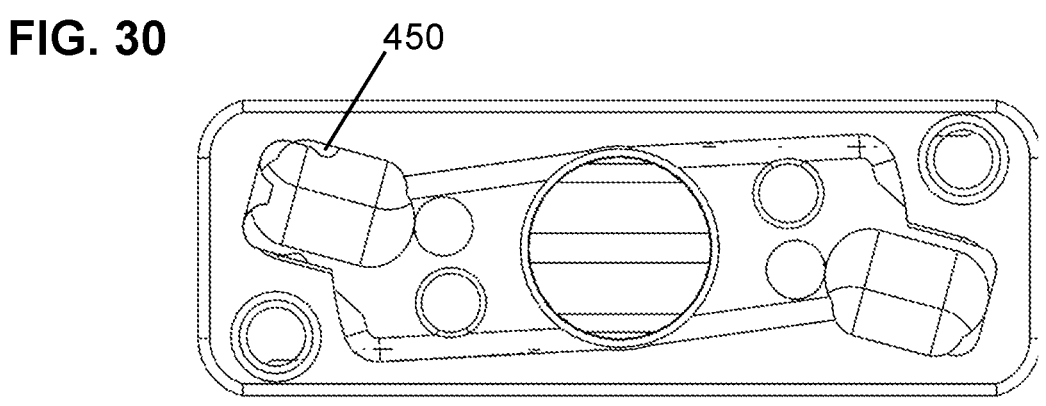

The retention clips 400 and 450 may be made from Nitinol per ASTM F2063 or another material that possesses shape memory but this is not a requirement in that those of skill in the art can create retention clips from other materials. One suggested process for inserting the cephalad retention clip 400 into the implant body 200 is shown in a sequence of steps in FIG. 28, FIG. 29, and FIG. 30. These views show the proximal face 110 of the implant body 200 including the cephalad blade sleeve tunnel 204. The process for inserting the caudal retention clip 450 would be analogous. One of skill in the art may devise another process to assemble the implant body with the retention clips 400 and 450 without deviating from the teachings of the present disclosure.

Locking Cam Material.

The locking cam 500 may be made from a titanium alloy (Ti-6Al-4V ELI) per ASTM F136 although one of skill in the art could select another material.

More than One Locking Cam.

Figure 31:
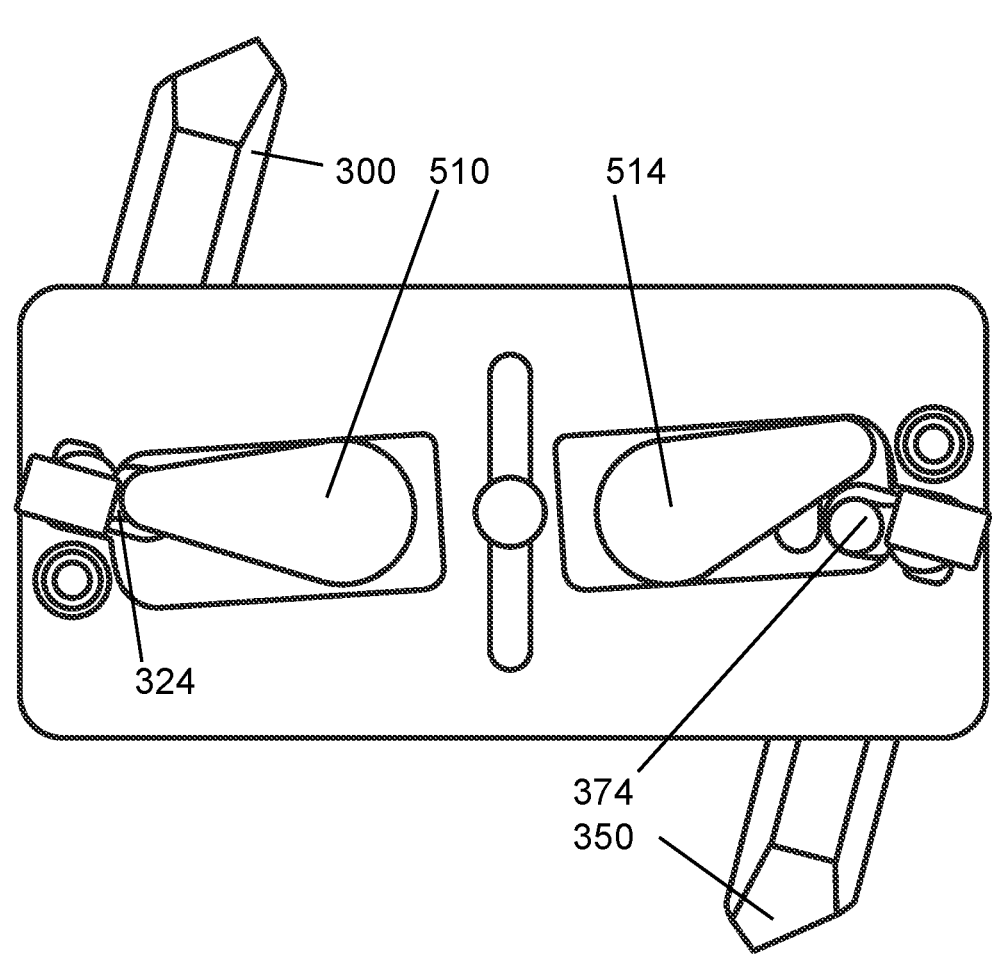
FIG. 31 shows fusion implant 920 that has not one but two locking cams.

The embodiment discussed at length above had one locking cam 500. Those of skill in the art appreciate that having fewer components to manufacture, assemble, and manipulate is often advantageous relative to having the same functionality through the use of more parts. FIG. 31 shows fusion implant 920 which is very much like fusion implant 100. Fusion implant 920 has a cephalad locking cam 510 shown here in the locked position that precludes proximal movement of the cephalad anchor blade 300 as lock plane 324 is at least partially covered by cephalad locking cam 510. Fusion implant 920 has a caudal locking cam 514 shown here in the unlocked position that does not preclude proximal movement of the caudal anchor blade 350 as lock plane 374 is not at least partially covered by caudal locking cam 514.

One of skill in the art will appreciate that if there are two different locking cams and the cephalad anchor blade is not driven into the deployed position at the same time as the caudal anchor blade is driven into the deployed position that a range of sequences are possible. Thus, an anchor blade and the corresponding locking may be driven and locked before the other anchor blade is driven. It is likely that both anchor blades will be driven into position before either anchor blade is locked but that is not a requirement of this disclosure.

Lateral or Posterior Approach.

One of skill in the art will appreciate that the teachings of the present application can be used with implants that are delivered to disc spaces on the spine through a variety of approaches—anterior, lateral, posterior, and oblique. The preferred option is at least partially a function of what disc space is being treated whether it is within the cervical, thoracic, or lumbar portion of the spine. One of skill in the art will recognize that the fusion implants described in this disclosure could be used in anterior cervical interbody fusion procedures in skeletally mature patients with degenerative disc disease at one disc level from C2-T1 but the teachings of the present disclosure could be used at other disc levels and through other approaches.

Cephalad Face and Caudal Face.

The cephalad face 130 and the caudal face 140 of the fusion implant 100 were shown to be substantially smooth and flat. This is not a requirement for use of the teachings of the present disclosure and other surfaces including those with recesses, protrusions, teeth, or other features may be used as is known in the art.

Interference Fit for Holding Anchor Blades.

The disclosure has taught the use of retention clips 400 and 450 to hold anchor blades 300 and 350 in the fusion implant 100 from before delivery into the operating room and through delivery to the intervertebral space. While one of skill in the art will appreciate the many benefits of this solution, one of skill in the art will recognize that with tight control over tolerances in the making of implant body 200 and of the anchor blades 300 and 350 that an interference fit could be substituted for the retention clips 400 and 450.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

Where methods and/or events described above indicate certain events and/or procedures occurring in a certain order, the ordering of certain events and/or procedures may be modified. Additionally, certain events and/or procedures may be performed concurrently in a parallel process when possible, as well as performed sequentially as described above.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. A fusion implant with pre-assembled anchor blades for delivery between adjacent vertebrae; the fusion implant comprising:
   an implant body;
   a cephalad anchor blade;
   a caudal anchor blade; and
   a set of at least one locking cam rotatably engaged with the implant body;
   the implant body having:
   a proximal face:
   a distal face opposite the proximal face;
   a cephalad face;
   a caudal face opposite the cephalad face;
   a right face between the proximal face and the distal face and between the cephalad face and the caudal face;
   a left face opposite the right face and between the proximal face and the distal face and between the cephalad face and the caudal face;
   the cephalad anchor blade comprising:
   a cephalad distal tip for penetration into cortical bone;
   a cephalad proximal end having:
   a cephalad lock plane for use in locking the cephalad anchor blade in a deployed position;

a cephalad stop plane facing distally which prevents the cephalad proximal end from traveling beyond the proximal face of the implant body into an interior of the implant body;

the cephalad distal tip and the cephalad proximal end located along a cephalad curved path such that the cephalad distal tip may be inserted into a cephalad blade sleeve tunnel at the proximal face and travel through the cephalad blade sleeve tunnel in the implant body to emerge from a cephalad sleeve tunnel egress opening on the cephalad face of the fusion implant and continue moving on the cephalad curved path until the cephalad stop plane contacts the proximal face of the fusion implant;

the cephalad anchor blade held in a delivery position pending delivery between adjacent vertebrae;

wherein application of sufficient pressure on the cephalad proximal end of the cephalad anchor blade is adequate to overcome a first interaction between the cephalad anchor blade and the implant body and cause a portion of the cephalad anchor blade to move through the cephalad sleeve tunnel egress opening;

the caudal anchor blade comprising:

a caudal distal tip for penetration into cortical bone;

a caudal proximal end having:

a caudal lock plane for use in locking the caudal anchor blade in a deployed position; and a caudal stop plane facing distally which prevents the caudal proximal end of the caudal anchor blade from traveling beyond the proximal face of the implant body into the interior of the implant body;

the caudal distal tip and the caudal proximal end located along a caudal curved path such that the caudal distal tip may be inserted into a caudal blade sleeve tunnel at the proximal face and travel through the caudal blade sleeve tunnel in the implant body to emerge from a caudal sleeve tunnel egress opening on the caudal face of the fusion implant and continue moving on the caudal curved path until the caudal stop plane contacts the proximal face of the fusion implant;

the caudal anchor blade held in a delivery position pending delivery between adjacent vertebrae;

wherein application of sufficient pressure on the caudal proximal end of the caudal anchor blade is adequate to overcome a second interaction between the caudal anchor blade and the implant body and cause a portion of the caudal anchor blade to move through caudal sleeve tunnel egress opening;

the set of at least one locking cam having a delivery position wherein the set of at least one locking cam does not limit:

movement of the cephalad anchor blade; or movement of the caudal anchor blade; and the set of at least one locking cam also having a locking position wherein:

the cephalad anchor blade that is in the deployed position cannot move the cephalad proximal end in a proximal direction away from the proximal face of the implant body; and the caudal anchor blade that is in the deployed position cannot move the caudal proximal end in a proximal direction away from the proximal face of the implant body.

2. The fusion implant of claim 1 wherein while the cephalad anchor blade is being held in the delivery position—the cephalad distal tip is within the cephalad blade sleeve tunnel and not extending beyond a cephalad anchor blade egress opening.

3. The fusion implant of claim 1 wherein while the caudal anchor blade is being held in the delivery position—the caudal distal tip is within the caudal blade sleeve tunnel and not extending beyond a caudal anchor blade egress opening.

4. The fusion implant of claim 1 wherein the fusion implant further comprises:

a cephalad retention clip; and a caudal retention clip; and the cephalad anchor blade further comprising:

a cephalad retention groove partway between the cephalad distal tip and the cephalad proximal end;

the cephalad retention groove positioned to engage with the cephalad retention clip via a first interaction to hold the cephalad anchor blade in the delivery position wherein the cephalad distal tip is within the cephalad blade sleeve tunnel and not extending beyond a cephalad anchor blade egress opening;

the first interaction of the cephalad retention groove and the cephalad retention clip adapted to allow the cephalad anchor blade to respond to pressure on the cephalad proximal end to overcome the first interaction and cause a portion of the cephalad anchor blade to move through the cephalad anchor blade egress opening;

the caudal anchor blade further comprising:

a caudal retention groove partway between the caudal distal tip and the caudal proximal end;

the caudal retention groove positioned to engage with the caudal retention clip via a second interaction to hold the caudal anchor blade in the delivery position wherein the caudal distal tip of the caudal anchor blade is within the caudal blade sleeve tunnel and not extending beyond a caudal anchor blade egress opening; and the second interaction of the caudal retention groove and the caudal retention clip adapted to allow the caudal anchor blade to respond to pressure on the caudal proximal end of the cephalad anchor blade to overcome the second interaction and cause a portion of the caudal anchor blade to move through the caudal anchor blade egress opening.

5. The fusion implant of claim 1 wherein the cephalad anchor blade is retained in the cephalad blade sleeve tunnel while the anchor blades are in the delivery position by a cephalad interference fit.

6. The fusion implant of claim 1 wherein the caudal anchor blade is retained in the caudal blade sleeve tunnel while the anchor blades are in the delivery position by a caudal interference fit.

7. The fusion implant of claim 6 wherein the cephalad anchor blade is retained in the cephalad blade sleeve tunnel while the anchor blades are in the delivery position by a cephalad interference fit.

8. The fusion implant of claim 1 wherein the set of at least one locking cam is a set of only one locking cam and a partial rotation of the locking cam rotates the locking cam from the delivery position to the locking position;

wherein the locking cam in the locking position traps the cephalad lock plane of the cephalad anchor blade so that the cephalad anchor blade is limited in ability for distal movement beyond the proximal face of the fusion implant by the cephalad stop plane and is limited in ability for further proximal movement by the locking cam contacting the cephalad lock plane; and wherein the locking cam in the locking position traps the caudal lock plane of the caudal anchor blade so that the caudal anchor blade is limited for further distal movement beyond the proximal face of the fusion implant by the caudal stop plane and is limited for further proximal movement by the locking cam contacting the caudal lock plane.

9. The fusion implant of claim 1 wherein the set of at least one locking cam is a set of a cephalad locking cam and a caudal locking cam;

a partial rotation of the cephalad locking cam rotates the cephalad locking cam from the delivery position to the locking position;

wherein the cephalad locking cam in the locking position traps the cephalad lock plane of the cephalad anchor blade so that the cephalad anchor blade is limited in ability for distal movement beyond the proximal face of the fusion implant by the cephalad stop plane and is limited in ability for further proximal movement by the cephalad locking cam contacting the cephalad lock plane; and a partial rotation of the caudal locking cam rotates the caudal locking cam from the delivery position to the locking position; and wherein the caudal locking cam in the locking position traps the caudal lock plane of the caudal anchor blade so that the caudal anchor blade is limited for further distal movement beyond the proximal face of the fusion implant by the caudal stop plane and is limited for further proximal movement by the caudal locking cam contacting the caudal lock plane.

10. The fusion implant of claim 1 further comprising a bone growth conduit with an opening on the cephalad face of the fusion implant and a second opening on the caudal face of the fusion implant.

11. The fusion implant of claim 1 wherein the implant body is created using additive manufacturing so that the cephalad blade sleeve tunnel substantially surrounds a portion of the cephalad anchor blade within the implant body.

12. The fusion implant of claim 1 wherein the cephalad blade sleeve tunnel has a series of cross sections taken perpendicular to a midline of the cephalad blade sleeve tunnel and a majority of the series of cross sections are solid so that at that cross section of the cephalad blade sleeve tunnel, the cephalad anchor blade is totally surrounded by that cross section of the cephalad blade sleeve tunnel.

13. The fusion implant of claim 1 wherein the implant body is created using additive manufacturing so that the caudal blade sleeve tunnel substantially surrounds a portion of the caudal anchor blade within the implant body.

14. The fusion implant of claim 13 wherein the caudal blade sleeve tunnel has a series of cross sections taken perpendicular to a midline of the caudal blade sleeve tunnel and a majority of the series of cross sections are solid so that at that cross section of the caudal blade sleeve tunnel, the caudal anchor blade is totally surrounded by that cross section of the caudal blade sleeve tunnel.

15. The fusion implant of claim 1 wherein the implant body is created using additive manufacturing so that the cephalad blade sleeve tunnel totally encircles the cephalad anchor blade.

16. The fusion implant of claim 1 wherein the implant body is created using additive manufacturing so that the cephalad blade sleeve tunnel is substantially solid on both a right side and a left side of the cephalad blade sleeve tunnel.

17. A fusion implant with a cephalad anchor blade and a caudal anchor blade held within the fusion implant in a delivery position before removal from sterilized packaging, the fusion implant comprising:

an implant body;

18 the cephalad anchor blade for extending into a cephalad vertebra after the fusion implant is delivered between the cephalad vertebra and a caudal vertebra;

the caudal anchor blade for extending into the caudal vertebra after the fusion implant is delivered between the cephalad vertebra and the caudal vertebra;

the cephalad anchor blade having a cephalad proximal end comprising:

a cephalad lock plane for use in locking the cephalad anchor blade in a deployed position;

a cephalad stop plane facing distally which prevents the cephalad proximal end from traveling beyond a proximal face of the implant body into an interior of the implant body;

the caudal anchor blade having a caudal proximal end comprising:

a caudal lock plane for use in locking the caudal anchor blade in a deployed position; and a caudal stop plane facing distally which prevents the caudal proximal end of the caudal anchor blade from traveling beyond the proximal face of the implant body into the interior of the implant body;

a set of at least one locking cam rotatably engaged with the implant body;

each of the set of at least one locking cam having a delivery position wherein each the set of at least one locking cam does not limit:

movement of the cephalad anchor blade; or movement of the caudal anchor blade; and each of the set of at least one locking cam also having a locking position wherein:

the cephalad anchor blade that is in the deployed position cannot move the cephalad proximal end in a proximal direction away from the proximal face of the implant body; and the caudal anchor blade that is in the deployed position cannot move the caudal proximal end in a proximal direction away from the proximal face of the implant body.

18. The fusion implant of claim 17 wherein:

a cephalad locking cam once moved into the locking position traps the cephalad lock plane of the cephalad anchor blade so that the cephalad anchor blade is limited in ability for distal movement beyond the proximal face of the fusion implant by the cephalad stop plane and is limited in ability for further proximal movement by the cephalad locking cam contacting the cephalad lock plane; and wherein a caudal locking cam in the locking position traps the caudal lock plane of the caudal anchor blade so that the caudal anchor blade is limited for further distal movement beyond the proximal face of the fusion implant by the caudal stop plane and is limited for further proximal movement by the caudal locking cam contacting the caudal lock plane.

19. The fusion implant of claim 18 wherein the set of at least one locking cam has a single locking cam that serves as the cephalad locking cam and the caudal locking cam.

20. The fusion implant of claim 18 wherein the set of at least one locking cam has the cephalad locking cam and the caudal locking cam and the cephalad locking cam is not part of the caudal locking cam.

21. The fusion implant of claim 17 wherein the set of at least one locking cam has at least one arm to hold one of the anchor blades selected from the cephalad anchor blade and the caudal anchor blade in the deployed position and the set of at least one locking cam moves the at least one arm less than 360 degrees from the delivery position to the locked position.

22. A fusion implant comprising:

an implant body;

a cephalad anchor blade for extending into a cephalad vertebra after the fusion implant is delivered between the cephalad vertebra and a caudal vertebra;

the cephalad anchor blade having a cephalad retention groove partway between a cephalad distal tip and a cephalad proximal end; the cephalad retention groove positioned to engage with a cephalad retention clip via a first interaction to hold the cephalad anchor blade in a delivery position wherein the cephalad distal tip is within a cephalad blade sleeve tunnel and not extending beyond a cephalad anchor blade egress opening;

the first interaction of the cephalad retention groove and the cephalad retention clip adapted to allow the cephalad anchor blade to respond to pressure on the cephalad proximal end to overcome the first interaction and cause a portion of the cephalad anchor blade to extend into the cephalad vertebra;

a caudal anchor blade for extending into the caudal vertebra after the fusion implant is delivered between the cephalad vertebra and the caudal vertebra;

the caudal anchor blade having a caudal retention groove partway between a caudal distal tip and a caudal proximal end;

the caudal retention groove positioned to engage with a caudal retention clip via a second interaction to hold the caudal anchor blade in a delivery position wherein the caudal distal tip of the caudal anchor blade is within a caudal blade sleeve tunnel and not extending beyond a caudal anchor blade egress opening; and the second interaction of the caudal retention groove and the caudal retention clip adapted to allow the caudal anchor blade to respond to pressure on the caudal proximal end of the cephalad anchor blade to overcome the second interaction and cause a portion of the caudal anchor blade to extend into the caudal vertebra.

23. The fusion implant of claim 22 wherein the cephalad anchor blade responds to pressure on the cephalad proximal end to:

1) Overcome the first interaction and cause the portion of the cephalad anchor blade to extend into the cephalad vertebra; and 2) Cause a distal tip of the cephalad anchor blade to be advanced and extend beyond a cephalad face of the implant body as the distal tip of the cephalad anchor blade is recessed within the fusion implant while the cephalad anchor blade is in the delivery position.

24. The fusion implant of claim 22 wherein the caudal anchor blade responds to pressure on the caudal proximal end to:

1) Overcome the second interaction and cause the portion of the caudal anchor blade to extend into the caudal vertebra; and 2) Cause a distal tip of the caudal anchor blade to be advanced and extend beyond a caudal face of the implant body as the distal tip of the caudal anchor blade is recessed within the fusion implant while the caudal anchor blade is in the delivery position.

25. A fusion implant for placement between adjacent vertebrae; the fusing implant comprising:

an implant body;

a cephalad anchor blade;

a caudal anchor blade;

a cephalad retention clip;

a caudal retention clip; and a locking cam rotatably engaged with the implant body;

the implant body having:

a proximal face:

a distal face opposite the proximal face;

a cephalad face;

a caudal face opposite the cephalad face;

a right face between the proximal face and the distal face and between the cephalad face and the caudal face;

a left face opposite the right face and between the proximal face and the distal face and between the cephalad face and the caudal face;

the cephalad anchor blade comprising:

a cephalad distal tip for penetration into cortical bone;

a cephalad proximal end having:

a cephalad lock plane for use in locking the cephalad anchor blade in a deployed position;

a cephalad stop plane facing distally which prevents the cephalad proximal end from traveling beyond the proximal face of the implant body into an interior of the implant body;

the cephalad distal tip and the cephalad proximal end located along a cephalad curved path such that the cephalad distal tip may be inserted into a cephalad blade sleeve tunnel at the proximal face and travel through the cephalad blade sleeve tunnel in the implant body to emerge from a cephalad sleeve tunnel egress opening on the cephalad face of the fusion implant and continue moving on the cephalad curved path until the cephalad stop plane contacts the proximal face of the fusion implant;

a cephalad retention groove partway between the cephalad distal tip and the cephalad proximal end; the cephalad retention groove positioned to engage with the cephalad retention clip via a first interaction to hold the cephalad anchor blade in a delivery position wherein the cephalad distal tip is within the cephalad blade sleeve tunnel and not extending beyond a cephalad anchor blade egress opening;

the first interaction of the cephalad retention groove and the cephalad retention clip adapted to allow the cephalad anchor blade to respond to pressure on the cephalad proximal end to overcome the first interaction and cause a portion of the cephalad anchor blade to move through the cephalad anchor blade egress opening;

the caudal anchor blade comprising:

a caudal distal tip for penetration into cortical bone;

a caudal proximal end having:

a caudal lock plane for use in locking the caudal anchor blade in a deployed position; and a caudal stop plane facing distally which prevents the caudal proximal end of the caudal anchor blade from traveling beyond the proximal face of the implant body into the interior of the implant body;

the caudal distal tip and the caudal proximal end located along a caudal curved path such that the caudal distal tip may be inserted into a caudal blade sleeve tunnel at the proximal face and travel through the caudal blade sleeve tunnel in the implant body to emerge from a caudal sleeve tunnel egress opening on the caudal face of the fusion implant and continue moving on the caudal curved path until the caudal stop plane contacts the proximal face of the fusion implant;

a caudal retention groove partway between the caudal distal tip and the caudal proximal end;

the caudal retention groove positioned to engage with the caudal retention clip via a second interaction to hold the caudal anchor blade in a delivery position wherein the caudal distal tip of the caudal anchor blade is within the caudal blade sleeve tunnel and not extending beyond a caudal anchor blade egress opening;

the second interaction of the caudal retention groove and the caudal retention clip adapted to allow the caudal anchor blade to respond to pressure on the caudal proximal end of the cephalad anchor blade to overcome the second interaction and cause a portion of the caudal anchor blade to move through the caudal anchor blade egress opening;

the locking cam having a delivery position wherein the locking cam does not limit:

movement of the cephalad anchor blade; or
    movement of the caudal anchor blade; and
the locking cam also having a locking position wherein
    the cephalad anchor blade that is in the deployed position cannot move the cephalad proximal end in a proximal direction away from the proximal face of the implant body; and
    the caudal anchor blade that is in the deployed position cannot move the caudal proximal end in a proximal direction away from the proximal face of the implant body.

26. A fusion implant for placement between adjacent vertebrae; the fusing implant comprising:
    an implant body;
    a cephalad anchor blade;
    a caudal anchor blade;
    and
    a locking cam rotatably engaged with the implant body;
the implant body having:
    a proximal face:
    a distal face opposite the proximal face;
    a cephalad face;
    a caudal face opposite the cephalad face;
    a right face between the proximal face and the distal face and between the cephalad face and the caudal face;
    a left face opposite the right face and between the proximal face and the distal face and between the cephalad face and the caudal face;
the cephalad anchor blade comprising:
    a cephalad distal tip for penetration into cortical bone;
    a cephalad proximal end having:
        a cephalad lock plane for use in locking the cephalad anchor blade in a deployed position;
        a cephalad stop plane facing distally which prevents the cephalad proximal end from traveling beyond the proximal face of the implant body into an interior of the implant body;
the cephalad distal tip and the cephalad proximal end located along a cephalad curved path such that the cephalad distal tip may be inserted into a cephalad blade sleeve tunnel at the proximal face and travel through the cephalad blade sleeve tunnel in the implant body to emerge from a cephalad sleeve tunnel egress opening on the cephalad face of the fusion implant and continue moving on the cephalad curved path until the cephalad stop plane contacts the proximal face of the fusion implant;
the caudal anchor blade comprising:
    a caudal distal tip for penetration into cortical bone;
    a caudal proximal end having:
        a caudal lock plane for use in locking the caudal anchor blade in a deployed position; and a caudal stop plane facing distally which prevents the caudal proximal end of the caudal anchor blade from traveling beyond the proximal face of the implant body into the interior of the implant body;
    the caudal distal tip and the caudal proximal end located along a caudal curved path such that the caudal distal tip may be inserted into a caudal blade sleeve tunnel at the proximal face and travel through the caudal blade sleeve tunnel in the implant body to emerge from a caudal sleeve tunnel egress opening on the caudal face of the fusion implant and continue moving on the caudal curved path until the caudal stop plane contacts the proximal face of the fusion implant;
the locking cam having a delivery position wherein the locking cam does not limit:
    movement of the cephalad anchor blade; or
    movement of the caudal anchor blade; and
the locking cam also having a locking position wherein
    the cephalad anchor blade that is in the deployed position cannot move the cephalad proximal end in a proximal direction away from the proximal face of the implant body; and
    the caudal anchor blade that is in the deployed position cannot move the caudal proximal end in a proximal direction away from the proximal face of the implant body.

27. The fusion implant of claim 26 wherein the locking cam has at least one arm to hold one of the anchor blades selected from the cephalad anchor blade and the caudal anchor blade in the deployed position and the locking cam moves the at least one arm less than 360 degrees from the delivery position to the locked position.

28. A fusion implant (100, 904, 908, 920) pre-assembled with a pair of anchor blades (300, 350) for delivery between adjacent vertebrae while the pair of anchor blades (300, 350) are in a delivery position;
    the fusion implant (100, 904, 908, 920) comprising:
        an implant body (200);
        a cephalad anchor blade (300);
        a caudal anchor blade (350);
        and
        a set of at least one locking cam (500, 510, 514) rotatably engaged with the implant body (200);
    the implant body (200) having:
        a proximal face (110);
        a distal face (120) opposite the proximal face (110);
        a cephalad face (130);
        a caudal face (140) opposite the cephalad face (130);
        a right face (150) between the proximal face (110) and the distal face (120) and between the cephalad face (130) and the caudal face (140);
        a left face (160) opposite the right face (150) and between the proximal face (110) and the distal face (120) and between the cephalad face (130) and the caudal face (140);
    the cephalad anchor blade (300) comprising:
        a cephalad distal tip (304) for penetration into cortical bone;
        a cephalad proximal end having:
            a cephalad lock plane (324) for use in locking the cephalad anchor blade (300) in a deployed position;
            a cephalad stop plane (314) facing distally which prevents the cephalad proximal end from traveling beyond the proximal face (110) of the implant body (200) into an interior of the implant body (200);

the cephalad distal tip (304) and the cephalad proximal end located along a cephalad curved path such that the cephalad distal tip (304) may be inserted into a cephalad blade sleeve tunnel (204) at the proximal face (110) and travel through the cephalad blade sleeve tunnel (204) in the implant body (200) to emerge from a cephalad sleeve tunnel egress opening (208) on the cephalad face (130) of the fusion implant (100, 904, 908, 920) and continue moving on the cephalad curved path until the cephalad stop plane (314) contacts the proximal face (110) of the fusion implant (100, 904, 908, 920);

the cephalad anchor blade (300) held in the delivery position pending delivery between adjacent vertebrae;

wherein application of sufficient pressure on the cephalad proximal end of the cephalad anchor blade (300) is adequate to overcome a first interaction between the cephalad anchor blade (300) and the implant body (200) and cause a portion of the cephalad anchor blade (300) to move through the cephalad sleeve tunnel egress opening (208);

the caudal anchor blade (350) comprising:

a caudal distal tip (354) for penetration into cortical bone;

a caudal proximal end having:

a caudal lock plane (374) for use in locking the caudal anchor blade (350) in a deployed position; and a caudal stop plane (364) facing distally which prevents the caudal proximal end of the caudal anchor blade (350) from traveling beyond the proximal face (110) of the implant body (200) into the interior of the implant body (200);

the caudal distal tip (354) and the caudal proximal end located along a caudal curved path such that the caudal distal tip (354) may be inserted into a caudal blade sleeve tunnel (254) at the proximal face (110) and travel through the caudal blade sleeve tunnel (254) in the implant body (200) to emerge from a caudal sleeve tunnel egress opening (258) on the caudal face (140) of the fusion implant (100, 904, 908, 920) and continue moving on the caudal curved path until the caudal stop plane (364) contacts the proximal face (110) of the fusion implant (100, 904, 908, 920);

the caudal anchor blade (350) held in the delivery position pending delivery between adjacent vertebrae;

wherein application of sufficient pressure on the caudal proximal end of the caudal anchor blade (350) is adequate to overcome a second interaction between the caudal anchor blade (350) and the implant body (200) and cause a portion of the caudal anchor blade (350) to move through the caudal sleeve tunnel egress opening (258);

the set of at least one locking cam (500, 510, 514) having a delivery position wherein the set of at least one locking cam (500, 510, 514) does not limit:

movement of the cephalad anchor blade (300); or movement of the caudal anchor blade (350); and the set of at least one locking cam (500, 510, 514) also having a locking position wherein:

the cephalad anchor blade (300) that is in the deployed position cannot move the cephalad proximal end in a proximal direction away from the proximal face (110) of the implant body (200); and the caudal anchor blade (350) that is in the deployed position cannot move the caudal proximal end in a proximal direction away from the proximal face (110) of the implant body (200);

the fusion implant (100, 904, 908, 920) further comprising:

a cephalad retention clip (400); and a caudal retention clip (450); and the cephalad anchor blade (300) further comprising:

a cephalad retention groove (330) partway between the cephalad distal tip (304) and the cephalad proximal end;

the cephalad retention groove (330) positioned to engage with the cephalad retention clip (400) via a first interaction to hold the cephalad anchor blade (300) in the delivery position wherein the cephalad distal tip (304) is within the cephalad blade sleeve tunnel (204) and not extending beyond a cephalad sleeve tunnel egress opening (208);

the first interaction of the cephalad retention groove (330) and the cephalad retention clip (400) adapted to allow the cephalad anchor blade (300) to respond to pressure on the cephalad proximal end to overcome the first interaction and cause a portion of the cephalad anchor blade (300) to move through the cephalad sleeve tunnel egress opening (208);

the caudal anchor blade (350) further comprising:

a caudal retention groove (380) partway between the caudal distal tip (354) and the caudal proximal end;

the caudal retention groove (380) positioned to engage with the caudal retention clip (450) via a second interaction to hold the caudal anchor blade (350) in the delivery position wherein the caudal distal tip (354) of the caudal anchor blade (350) is within the caudal blade sleeve tunnel (254) and not extending beyond a caudal sleeve tunnel egress opening (258); and the second interaction of the caudal retention groove (380) and the caudal retention clip (450) adapted to allow the caudal anchor blade (350) to respond to pressure on the caudal proximal end of the caudal anchor blade (350) to overcome the second interaction and cause a portion of the caudal anchor blade (350) to move through the caudal sleeve tunnel egress opening (258).

29. The fusion implant of claim 28 wherein the set of at least one locking cam is a set of only one locking cam (500) and a partial rotation of the locking cam rotates the locking cam from the delivery position to the locking position;

wherein the locking cam in the locking position traps the cephalad lock plane (324) of the cephalad anchor blade so that the cephalad anchor blade is limited in ability for distal movement beyond the proximal face of the fusion implant by the cephalad stop plane and is limited in ability for further proximal movement by the locking cam contacting the cephalad lock plane; and wherein the locking cam in the locking position traps the caudal lock plane (374) of the caudal anchor blade so that the caudal anchor blade is limited for further distal movement beyond the proximal face of the fusion implant by the caudal stop plane and is limited for further proximal movement by the locking cam contacting the caudal lock plane.

30. The fusion implant of claim 28 wherein the set of at least one locking cam is a set of a cephalad locking cam (510) and a caudal locking cam 514);

a partial rotation of the cephalad locking cam rotates the cephalad locking cam from the delivery position to the locking position;

wherein the cephalad locking cam in the locking position traps the cephalad lock plane (324) of the cephalad anchor blade so that the cephalad anchor blade is limited in ability for distal movement beyond the proximal face of the fusion implant by the cephalad stop plane and is limited in ability for further proximal movement by the cephalad locking cam contacting the cephalad lock plane; and a partial rotation of the caudal locking cam rotates the caudal locking cam from the delivery position to the locking position; and wherein the caudal locking cam in the locking position traps the caudal lock plane (374) of the caudal anchor blade so that the caudal anchor blade is limited for further distal movement beyond the proximal face of the fusion implant by the caudal stop plane and is limited for further proximal movement by the caudal locking cam contacting the caudal lock plane.

31. The fusion implant of claim 28 wherein the implant body is created using additive manufacturing so that the cephalad blade sleeve tunnel substantially surrounds a portion of the cephalad anchor blade within the implant body.

32. The fusion implant of claim 28 wherein the cephalad blade sleeve tunnel has a series of cross sections taken perpendicular to a midline of the cephalad blade sleeve tunnel and a majority of the series of cross sections are solid so that at that cross section of the cephalad blade sleeve tunnel, the cephalad anchor blade is totally surrounded by that cross section of the cephalad blade sleeve tunnel.

33. The fusion implant of claim 28 wherein the implant body is created using additive manufacturing so that the caudal blade sleeve tunnel substantially surrounds a portion of the caudal anchor blade within the implant body.

34. The fusion implant of claim 33 wherein the caudal blade sleeve tunnel has a series of cross sections taken perpendicular to a midline of the caudal blade sleeve tunnel and a majority of the series of cross sections are solid so that at that cross section of the caudal blade sleeve tunnel, the caudal anchor blade is totally surrounded by that cross section of the caudal blade sleeve tunnel.

35. A fusion implant assembly with at least a first anchor blade that is configured to extend into a first vertebral body comprising:

an implant body with at least a first internal passageway that allows a first distal tip of the first anchor blade to move from a first face of the implant body out a second face of the implant body different from the first face, the second face configured to be oriented towards the first vertebral body;

a first locking cam rotatably engaged with the implant body so that the first locking cam can rotate less than 360 degrees to move from a first deployment position to a first locked position; and the first anchor blade having:
the first distal tip;
a first stop plane to limit forward movement of the first distal tip; and;
a first locking plane to be locked in place by the first locking cam when the first locking cam is rotated to the first locking position so that the first distal tip cannot move back towards the implant body.

36. The fusion implant assembly of claim 35 further comprising:

a second internal passageway in the implant body that allows a second distal tip of a second anchor blade to move from the first face of the implant body out a third face of the implant body different from the first face and the third face configured to be oriented towards a second vertebral body different from the first vertebral body; and the second anchor blade having:
the second distal tip;
a second stop plane to limit forward movement of the second distal tip; and;
a second locking plane to be locked in place by the first locking cam when the first locking cam is rotated to the first locking position so that the second distal tip cannot move back towards the implant body.

37. The fusion implant assembly of claim 35 further comprising:

a second internal passageway in the implant body that allows a second distal tip of a second anchor blade to move from the first face of the implant body out a third face of the implant body different from the first face and the third face configured to be oriented towards a second vertebral body different from the first vertebral body; and a second locking cam different from the first locking cam and rotatably engaged with the implant body so that the second locking cam can rotate less than 360 degrees to move from a second deployment position to a second locked position; and the second anchor blade having:
the second distal tip;
a second stop plane to limit forward movement of the second distal tip; and;
a second locking plane to be locked in place by the second locking cam when the second locking cam is rotated to the second locking position so that the second distal tip cannot move back towards the implant body.

38. A process to deploy a fusion implant with anchor blades and then lock the anchor blades in a deployed position, the process comprising:

opening a container and removing the fusion implant of claim 1 having the cephalad anchor blade and the caudal anchor blade which are both held in the delivery position for delivery between a cephalad vertebra and a caudal vertebra;

positioning the fusion implant between the cephalad vertebra and the caudal vertebra while the cephalad anchor blade and the caudal anchor blade are both held in the delivery position;

advancing the cephalad anchor blade into the deployed position which engages the cephalad vertebra;

advancing the caudal anchor blade into the deployed position which engages the caudal vertebra;

using the set of at least one locking cam:
to lock the cephalad anchor blade in the deployed position; and
to lock the caudal anchor blade in the deployed position; and wherein the cephalad anchor blade is held in the delivery position for delivery between the cephalad vertebra and the caudal vertebra by a cephalad locking clip that engages with a cephalad retention groove in the cephalad anchor blade.

39. The process of claim 38 wherein a single locking cam serves:

to lock the cephalad anchor blade in the deployed position; and
to lock the caudal anchor blade in the deployed position.

40. The process of claim 38 wherein the set of at least one locking cam comprises
a cephalad locking cam and a caudal locking cam different from the cephalad locking cam.

41. The process of claim 38 wherein the advancing the cephalad anchor blade into the deployed position which engages the cephalad vertebra and advancing the caudal anchor blade into the deployed position which engages the caudal vertebra happens at one time.

42. The process of claim 38 wherein advancing the cephalad anchor blade into the deployed position which engages the cephalad vertebra includes causing the cephalad locking clip to disengage from the cephalad retention groove in the cephalad anchor blade.

43. A process to deploy a fusion implant with anchor blades and then lock the anchor blades in a deployed position, the process comprising:

opening a container and removing the fusion implant of claim 1 which already has the cephalad anchor blade and the caudal anchor blade both held in the delivery position for delivery between a cephalad vertebra and a caudal vertebra;

positioning the fusion implant between the cephalad vertebra and the caudal vertebra while the cephalad anchor blade and the caudal anchor blade are both held in the delivery position;

advancing the cephalad anchor blade into the deployed position which engages the cephalad vertebra;

advancing the caudal anchor blade into the deployed position which engages the caudal vertebra;

wherein the set of at least one locking cam has a cephalad locking cam and a caudal locking cam;

using the cephalad locking cam to lock the cephalad anchor blade in the deployed position; and using the caudal locking cam to lock the caudal anchor blade in the deployed position; and wherein the cephalad anchor blade is held in the delivery position for delivery between the cephalad vertebra and the caudal vertebra by an interference fit between a portion of the cephalad anchor blade and the fusion implant.

* * * * *